(12) United States Patent
Nouvel

(10) Patent No.: US 8,871,806 B2
(45) Date of Patent: *Oct. 28, 2014

(54) METHODS FOR PREVENTING FLEA ALLERGY DERMATITIS IN COMPANION ANIMALS

(75) Inventor: Larry Nouvel, Plano, TX (US)

(73) Assignee: Sergeant's Pet Care Products, Inc., Omaha, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/490,213

(22) Filed: Jun. 6, 2012

(65) Prior Publication Data

US 2013/0331418 A1 Dec. 12, 2013

(51) Int. Cl.
  *A61K 31/275* (2006.01)
  *A01N 37/34* (2006.01)
  *A01N 53/00* (2006.01)
  *A61K 9/00* (2006.01)

(52) U.S. Cl.
  CPC ............... *A01N 53/00* (2013.01); *A61K 9/0017* (2013.01)
  USPC ............ 514/521; 514/345; 514/407; 514/520

(58) Field of Classification Search
  CPC ....... A01N 53/00; A01N 47/02; A01N 65/00; A01N 25/05; A01N 25/32; A61K 2300/00; A61K 9/0017; A61K 31/08; A61K 31/231; A61K 31/277; A61K 31/355; A61K 31/365; A61K 31/455
  USPC .................................. 514/345, 407, 520, 521
  See application file for complete search history.

(56) References Cited

U.S. PATENT DOCUMENTS

| 5,942,525 | A | 8/1999 | Pennington et al. | |
|---|---|---|---|---|
| 8,614,244 | B2 * | 12/2013 | Nouvel | 514/407 |
| 8,617,582 | B2 * | 12/2013 | Nouvel | 424/405 |
| 8,637,060 | B2 * | 1/2014 | Nouvel | 424/405 |
| 2007/0259834 | A1 | 11/2007 | Sirinyan et al. | |
| 2010/0075956 | A1 | 3/2010 | Critcher et al. | |
| 2011/0086890 | A1 * | 4/2011 | Kelley | 514/345 |
| 2011/0092560 | A1 | 4/2011 | Del Bigio | |
| 2012/0022111 | A1 | 1/2012 | Nouvel | |
| 2012/0029025 | A1 * | 2/2012 | Nouvel | 514/337 |
| 2012/0029033 | A1 * | 2/2012 | Nouvel | 514/345 |

FOREIGN PATENT DOCUMENTS

| WO | 2005015995 | 2/2005 |
|---|---|---|
| WO | WO2005/015995 | 2/2005 |

OTHER PUBLICATIONS

Dryden, Flea and tick control in the 21st century: challenges and opportunities, Veterinary Dermatology, 20:435-440 (2009).

\* cited by examiner

*Primary Examiner* — My-Chau T Tran
(74) *Attorney, Agent, or Firm* — Polsinelli PC

(57) ABSTRACT

Methods for reducing the incidence of flea allergy dermatitis (FAD) in a companion animal are disclosed, the methods directed to inhibiting blood feeding by ectoparasites on a companion animal. The methods of the present invention involve administering a pesticide composition comprising cyphenothrin to a companion animal, specifically dogs and cats, in doses and proportions which are parasiticidally effective against a variety of ectoparasites, and in formulations which are convenient for topical application to the animal's skin, preferably localized over a small surface area. Such methods are useful in preventing and/or reducing the incidence of flea allergy dermatitis.

34 Claims, No Drawings

METHODS FOR PREVENTING FLEA ALLERGY DERMATITIS IN COMPANION ANIMALS

FIELD OF THE INVENTION

The present invention provides methods for reducing the incidence of flea allergy dermatitis (FAD) in a companion animal. Specifically the present invention provides methods for inhibiting blood feeding by ectoparasites on a companion animal by administering to the companion animal a composition comprising cyphenothrin.

BACKGROUND OF THE INVENTION

There are more than 2,200 species of fleas recognized worldwide. In North America, only a few species commonly infest dogs and cats: *Ctenocephalides felis* (the cat flea), *C. canis* (the dog flea), *Pulex simulans* (a flea of small mammals), and *Echidnophaga gallinacea* (the poultry sticktight flea). The most prevalent flea infesting dogs and cats is the cat flea (*Ctenocephalides felis*). Cat fleas are responsible for flea allergy dermatitis.

Flea allergy dermatitis (FAD), or flea bite hypersensitivity, is an immunologic disorder and the most common dermatological disease in domestic animals, specifically dogs and cats. FAD exhibits as a very itchy skin reaction or allergy and predisposes to the development of secondary skin infections and diseases. For instance, FAD is one of the major causes of feline miliary dermatitis in cats (also known as miliary eczema, papulocrusting dermatitis or scabby cat disease). FAD is caused by flea bites, specifically the saliva of the flea, which contains many antigenic materials such as amino acids, aromatic compounds, polypeptides, and phosphorous. Dogs and cats can develop flea saliva allergies at any point in their life, and once they have it, it is seldom rectified.

Adult cat fleas begin feeding almost immediately once they find a host, with many fleas feeding within minutes. Feeding is so rapid that partially digested blood can be defecated in as little as just a few minutes after fleas acquire a host. While initiation of feeding is rapid, daily blood consumption is voracious. Female cat fleas can consume up to 10 times their body weight in blood on the very first day they are on the host and peak consumption occurs within a few days at 15 times their body weight daily (13.6 µL of blood per day). After rapid transit through the flea, the excreted blood dries within minutes into reddish black fecal pellets or long tubular coils ("flea dirt"). Fleas mate after feeding and egg production begins within 24-48 hours of females taking their first blood meal. Female cat fleas can produce up to 40-50 eggs/day during peak egg production, averaging 27 eggs/day through 50 days, and may continue to produce eggs for more than 100 days. See "Fleas and Flea Allergy Dermatitis: Introduction", The Merck Veterinary Manual, $9^{th}$ Edition, 2005; Dryden, "Flea and tick control in the $21^{st}$ century: challenges and opportunities", Veterinary Dermatology, DOI: 10.1111/j.1365-3164.2009.00838.x.

An indirect indicator of an insecticide's ability to reduce blood consumption by fleas is the ability of the compound to kill fleas before they are able to lay eggs, thereby reducing egg production. Not only is reduction in egg production an indicator of reduced blood consumption, it is also important for modern day flea control. Several adulticides, such as fipronil, imidacloprid, metaflumizone, mitenpyram, selamectin, and spinosad have had a major impact on reducing the occurrence of FAD in dogs and cats. However, these compounds neither sufficiently stop flea bites nor sufficiently stop flea feeding. Therefore, it is assumed that the role of these compounds in managing FAD is more related to a decrease in flea feeding over a prolonged period of time rather that eliminating flea biting from occurring at all.

Accordingly, it would be desirable to provide methods for preventing fleas from taking a blood meal on the host animal thereby reducing the incidence of or preventing flea allergy dermatitis from occurring in the host animal. In particular, a need exists for prophylaxis of flea allergy dermatitis.

SUMMARY OF THE INVENTION

The present invention is directed to the treatment and prevention of flea allergy dermatitis. Particularly, the present invention advantageously provides a method for reducing the incidence of flea allergy dermatitis induced by antigens found in flea saliva through the topical administration to a companion animal of an effective amount of a composition comprising cyphenothrin. The methods and compositions of the present invention provide for the inhibition of blood biting by fleas through the topical administration of compositions which repel fleas from taking a blood meal and depositing saliva onto the skin of the host animal before they die, which in turn decreases the incidence of flea allergy dermatitis occurring in the host animal.

One aspect of the present invention relates to the topical application of a composition comprising cyphenothrin to reduce the incidence of flea allergy dermatitis in a companion animal.

Another aspect of the present invention relates to the topical application of a composition comprising cyphenothrin to inhibit blood feeding by ectoparasites on a companion animal, wherein the inhibiting blood feeding results in the reduction in the incidence of flea allergy dermatitis in the companion animal.

Another aspect of the present invention relates to topical application of a composition comprising cyphenothrin as a prophylaxis of flea allergy dermatitis on an animal that has not yet developed flea allergy dermatitis.

Another aspect of the present invention relates to use of a composition comprising cyphenothrin as a treatment on an animal that has previously suffered or is currently suffering from flea allergy dermatitis.

All of the methods of the present invention encompass administering a localized cutaneous application between the shoulders of a companion animal, a composition comprising up to about 50% (w/w) cyphenothrin and about 50% to about 85% (w/w) organic solvent, wherein the composition is administered in a volume sufficient to deliver a dosage of cyphenothrin ranging from about 0.1 mg/kg to about 40 mg/kg of animal weight. The methods of the present invention reduce blood feeding by ectoparasites on the companion animal by at least 80% through administration of the composition to the animal.

Other aspects and iterations of the invention are detailed below.

DETAILED DESCRIPTION OF THE INVENTION

The present invention is directed to a method for treating and preventing flea allergy dermatitis. The compositions provided herein are pesticide compositions that comprise cyphenothrin in an amount up to about 50% by weight (preferably, between 20% and 55% by weight) to prevent flea allergy dermatitis in a companion animal. The method inhibits blood feeding by ectoparasites on a companion animal, such as dogs and cats. The present invention is based on the surprising and unexpected finding that treatment of a host animal with compositions of the invention results in preventing ectoparasites (such as fleas) from taking a blood meal before dying. By inhibiting blood biting by ectoparasites, the companion animal's risk for flea allergy dermatitis will be significantly reduced or even eliminated.

In addition to preventing flea allergy dermatitis by inhibiting blood feeding, the compositions disclosed herein further treat ectoparasite infestations of companion animals (such as dogs and cats), and also prevent future infestations by prolonged treatment efficacy that can last up to three months. As such, the compositions exterminate existing ectoparasites, and prevent those ectoparasites that survive from developing and reproducing. The compositions of the present invention halt the growth cycle and prevent ectoparasites from laying additional eggs and are useful in the treatment of many ectoparasites, especially fleas and ticks, found on domesticated animals. The compositions may further comprise an insect growth-regulating compound.

(a) Composition

The compositions of the present invention comprise cyphenothrin. Cyphenothrin is a member of a class of synthetic insecticides known as pyrethroids, which are related to naturally-occurring pyrethrins. Pyrethroids, in general, tend to be more effective than the natural pyrethrins and less toxic to mammals. Pyrethroids are axonic poisons that work by keeping the sodium channels open in the neuronal membranes. The sodium channel consists of a membrane protein with a hydrophilic interior which permits sodium ions to enter and exit the membrane. When the sodium channels are kept open, the influx of sodium ions results in hyperexcitation, and the pest becomes paralyzed.

Cyphenothrin is classified as a pyrethroid ester insecticide. Alternative names for cyphenothrin include: (RS)-α-cyano-3-phenoxybenzyl (1RS,3RS;1RS,3SR)-2,2-dimethyl-3-(2-methylprop-1-enyl)cyclopropanecarboxylate, d-trans-cyphenothrin, d-cyphenothrin, Gokilaht™, (RS)-α-cyano-3-phenoxybenzyl (1R)-cis-trans-2,2-dimethyl-3-(2-methylprop-1-enyl)cyclopropanecarboxylate, (RS)-α-cyano-3-phenoxybenzyl (RS)-cis-trans-chrysanthemate, and cyano(3-phenoxyphenyl)methyl 2,2-dimethyl-3-(2-methyl-1-propenyl)cyclopropanecarboxylate. Other suitable non-limiting examples of pyrethroids that can be used in the present invention include permethrin, cypermethrin, etofenprox, fenvalerate, and cyfluthrin.

In specific embodiments, the compositions of the present invention comprise of cyphenothrin as the sole pesticidal/acaricidal agent. In these embodiments, cyphenothrin comprises about 50%, 45%, 40%, 35%, 30%, 25%, 20%, 15%, 10%, 5%, or 1% (w/w) of the composition. For example, the amount of cyphenothrin present in the composition may range from between about 1% to about 50% (w/w) of the total composition, preferably ranges from about 20% to about 55% (w/w), and even more preferably ranges from between about 20% to about 30% (w/w) of the total composition. In one preferred embodiment, the amount of cyphenothrin present in the composition effective for inhibiting blood feeding of ectoparasites in dogs is about 20% (w/w) of the total composition.

In certain alternative embodiments, cyphenothrin may be combined with a second pesticidal/acaricidal agent to form the composition of the present invention, such as, for example, fipronil. Fipronil is a phenylpyrazole acaricide with efficacy against a broad spectrum of tick species and was first disclosed in U.S. Pat. No. 5,232,940. Fipronil achieves its efficacy by disrupting the central nervous system by blocking the passage of chloride ions through the GABA receptor and glutamate-gated chloride channels (GluCl), components of the central nervous system. This disruption causes hyperexcitation of contaminated nerves and muscles, which results in eventual death. Fipronil is a slow-acting acaricide, and as such, can be used to target not only the host, but also other ticks in which the host comes in contact. Alternative names for fipronil include: 5-amino-1-[2,6-dichloro-4-(trifluoromethyl)phenyl]-4-[(1-R,S)(trifluoromethyl)sulfinyl]-1H-pyrazole-3-carbonitrile, 5-amino-1-(2,6-dichloro-α,α,α-trifluoro-p-tolyl)-4-[(trifluoromethyl)sulfinyl]pyrazole-3-carbonitrile, and fluocyanobenpyrazole [CAS No. 120068-37-3]. Fipronil is generally available as either a liquid or solid crystalline substance or powder.

If cyphenothrin is used in combination with fipronil, fipronil typically comprises between about 1% and about 20% (w/w) of the total weight of the composition. In some embodiments, fipronil comprises up to about 20%, 19%, 18%, 17%, 16%, 15%, 14%, 13%, 12%, 11%, 10%, 9%, 8%, 7%, 6%, 5%, 4%, 3%, 2%, or 1% (w/w) of the composition. For example, the amount of fipronil present in a composition of the invention may range from between about 5% to about 15% (w/w) of the total composition, and preferably ranges from between about 7% and about 12% (w/w). Most preferably, the amount of fipronil present in the composition may range from between about 8% and about 11% (w/w) of the total composition. In an exemplary embodiment, the amount of fipronil present in the composition is 9.8% (w/w) of the total composition.

If cyphenothrin is used in combination with a second pesticidal/acaricidal agent, such as fipronil, cyphenothrin is then typically present in the composition at a lower concentration, preferably comprising between about 1% and about 30% (w/w) of the composition. In these alternative embodiments, cyphenothrin may comprise about 30%, 25%, 20%, 15%, 10%, 9%, 8%, 7%, 6%, 5%, or 1% (w/w) of the composition. For example, the amount of cyphenothrin present in a composition also comprising fipronil may range from between about 1% to about 18% (w/w) of the total composition, and preferably ranges from about 3% to about 16% (w/w). In another embodiment, the amount of cyphenothrin present in a composition also comprising fipronil may range from about 1% to about 10% (w/w) of the total composition weight. In a further embodiment, the amount of cyphenothrin present in a composition also comprising fipronil may range from about 20% to about 30% (w/w) of the total composition. In still another embodiment, the amount of cyphenothrin present in a composition may range from between about 5% to about 10% (w/w) of the total composition.

The composition of the current invention may additionally include an insect growth regulator (IGR). IGRs are known to not be effective in killing pre-existing ectoparasites; rather, they are frequently used to prevent reproduction, egg laying, and further infestation. An IGR is generally a compound that is capable of disrupting the growth and development of pest species, so that the pest cannot mature and reproduce. IGRs may include, but are not limited to juvenile hormone mimics, chitin synthesis inhibitors, and the like. Preferably, the IGR used in the present invention is a juvenile hormone mimic, such as dayoutong, epofenonane, fenoxycarb, hydroprene, kinoprene, methoprene, pyriproxyfen, or triprene. Alternatively, the IGR may be a chitin synthesis inhibitor, such as buprofezin, cyromazine, bistrifluoron, chlorbenzuron, chlorfluazuron, dichlorbenzuron, difluenzuron, flucycloxuron, flufenoxuron, hexaflumuron, lufenuron, novaluron, noviflumuron, penfluoron, teflubenzuron, or triflumuron. In a preferred embodiment, the insect growth regulator is pyriproxyfen, which also known as 4-phenoxyphenyl 2-(2-pyridyloxy) propyl ether and Nylar™.

If an IGR is added to the composition of the present invention, the IGR typically comprises less than about 10% (w/w) of the total weight of the composition, and preferably less than about 5% (w/w). In some embodiments, the IGR comprises about 10%, 9%, 8%, 7%, 6%, 5%, 4%, 3%, 2%, 1%, or 0.1% (w/w) of the composition. For example, the amount of IGR present in the composition may range from between 1% to about 5% (w/w) of the total composition, and preferably the IGR ranges from between about 1% to about 3% (w/w) of the total composition.

The compositions of the present invention, which are non-aqueous, also comprise an organic solvent. Generally, the organic solvent is defined as a carbon-containing chemical that is capable of dissolving a solid, liquid, or a gas. Although one skilled in the art will appreciate that a wide variety of solvents may be incorporated into the current invention, the solvents should generally have a dielectric constant ranging from about 1 to 40, a low boiling point (less than 100° C.), have a density less than the density of water (less than 1.0 at 20° C.), and generally be soluble with water. In addition, the organic solvent should cause minimal cutaneous irritation when applied to the skin of an animal, including a dog or cat. Suitable examples of organic solvents include, but are not limited to, acetyltributyl citrate, fatty acid esters such as dimethyl ester, diisobutyl adipate, acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, diethylene glycol monoethyl ether, purified diethylene glycol monoethyl ether, monomethylacetamide, dipropylene glycol monomethyl ether, liquid polyoxyethylene glycols, propylene glycol, 2-pyrrolidones such as N-methylpyrrolidone, diethylene glycol monoethyl ether, ethylene glycol, diethyl phthalate, ethoxydiglycol, or combinations thereof. In a preferred embodiment, the organic solvent comprises diethylene glycol monoethyl ether.

In addition, the organic solvent generally comprises between about 50% to about 85% (w/w) of the composition. In some embodiments, the organic solvent comprises about 85%, about 80%, about 75%, about 70%, about 65%, about 60%, about 55%, or about 50% (w/w) of the total composition. For example, the amount of organic solvent present in the composition preferably ranges from between about 60% to about 80% (w/w) of the composition. In another embodiment, the amount of organic solvent in the composition ranges from between about 60% to about 75% (w/w) of the total composition. In an additional embodiment, the amount of organic solvent in the composition ranges from between about 70% to 80% (w/w) of the total composition. In still another embodiment, the amount of organic solvent in the composition ranges from between about 65% to 70% (w/w). Many of the commercially-available topical compositions that incorporate a pyrethroid, including cyphenothrin, have reported that the animals suffer from adverse effects including paraesthesia (a skin sensation that generally comprises feelings of prickling, itching, and tingling). However, it has been shown that inclusion of solvent, particularly purified diethylene glycol monoethyl ether into a topical composition (such as a spot-on) helps to prevent the undesirable adverse effects associated with topical treatment regimens that include cyphenothrin, as further disclosed in U.S. Ser. No. 12/876,122 entitled LIQUID PEST CONTROL FORMULATION, which is commonly owned and is incorporated herein by reference.

The composition may further include an antioxidant. An antioxidant can generally be defined as a compound capable of slowing or preventing the oxidation of other molecules. Oxidation is a chemical reaction that transfers electrons from the original substance to an oxidizing agent. Oxidation reactions can produce free radicals, which start chain reactions that damage cells. Antioxidants terminate these chain reactions by removing free radical intermediates, and inhibit other oxidation reactions by being oxidized themselves. Within the composition, the antioxidant acts as a stabilizer, preventing the various components from degrading by oxidation processes.

Antioxidants incorporated into the current invention should generally be miscible with the organic solvents described herein. The antioxidant also should not cause irritation to the skin of an animal, specifically a dog or cat, when applied to the animal's skin. In addition, the antioxidant may be natural or synthetic. Suitable antioxidants include, but are not limited to, ascorbic acid and its salts, ascorbyl palmitate, ascorbyl stearate, anoxomer, N-acetylcysteine, benzyl isothiocyanate, m-aminobenzoic acid, o-aminobenzoic acid, p-aminobenzoic acid (PABA), butylated hydroxyanisole (BHA), butylated hydroxytoluene (BHT), caffeic acid, canthaxantin, alpha-carotene, beta-carotene, beta-carotene, beta-apo-carotenoic acid, carnosol, carvacrol, catechins, cetyl gallate, chlorogenic acid, citric acid and its salts, clove extract, coffee bean extract, p-coumaric acid, 3,4-dihydroxybenzoic acid, N,N'-diphenyl-p-phenylenediamine (DPPD), dilauryl thiodipropionate, distearyl thiodipropionate, 2,6-di-tert-butylphenol, dodecyl gallate, edetic acid, ellagic acid, erythorbic acid, sodium erythorbate, esculetin, esculin, 6-ethoxy-1, 2-dihydro-2,2,4-trimethylquinoline, ethyl gallate, ethyl maltol, ethylenediaminetetraacetic acid (EDTA), eucalyptus extract, eugenol, ferulic acid, flavonoids (e.g., catechin, epicatechin, epicatechin gallate, epigallocatechin (EGC), epigallocatechin gallate (EGCG), polyphenol epigallocatechin-3-gallate), flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinammic acid, hydroxyglutaric acid, hydroquinone, N-hydroxysuccinic acid, hydroxytryrosol, hydroxyurea, rice bran extract, lactic acid and its salts, lecithin, lecithin citrate; R-alpha-lipoic acid, lutein, lycopene, malic acid, maltol, 5-methoxy tryptamine, methyl gallate, monoglyceride citrate; monoisopropyl citrate; morin, beta-naphthoflavone, nordihydroguaiaretic acid (NDGA), octyl gallate, oxalic acid, palmityl citrate, phenothiazine, phosphatidylcholine, phosphoric acid, phosphates, phytic acid, phytylubichromel, pimento extract, propyl gallate, polyphosphates, quercetin, trans-resveratrol, rosemary extract, rosmarinic acid, sage extract, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and delta-tocotrienols), tyrosol, vanillic acid, 2,6-di-tert-butyl-4-hydroxymethylphenol (i.e., Ionox 100), 2,4-(tris-3',5'-bi-tert-butyl-4'-hydroxybenzyl)-mesitylene (i.e., Ionox 330), 2,4,5-trihydroxybutyrophenone, ubiquinone, tertiary butyl hydroquinone (TBHQ), thiodipropionic acid, trihydroxy butyrophenone, tryptamine, tyramine, uric acid, vitamin K and derivatives, vitamin Q10, wheat germ oil, zeaxanthin, or combinations thereof. One skilled in the art will appreciate that the antioxidants incorporated into the composition (including those listed herein) encompass all potential salt and ester forms of the antioxidants in addition to the pure forms of the compound. Preferably, the antioxidant comprises a vitamin E compound and may be selected from the group consisting of tocopherol acetate, tocopherol linoleate, tocopherol nicotinate, tocopherol succinate, ascorbyl tocopherol phosphate, dioleyl tocopherol methylsilanol, tocophersolan, tocopherol linoleate/oleate, and combinations thereof. In an exemplary embodiment, the antioxidant comprises tocopherol nicotinate [CAS No. 43119-47-7].

In addition, the antioxidant typically comprises less than about 10% (w/w) of the total composition. In some embodiments, the antioxidant comprises about 9%, 8%, 7%, 6%, 5%, 4%, 3%, 2%, 1%, 0.1%, or 0% (w/w) of the total composition. For example, the amount of antioxidant present in the composition may range from between 2% to about 10% (w/w) of the total composition, and preferably the antioxidant ranges from between about 3% to about 6% (w/w) of the total composition. In a further embodiment, the amount of antioxidant present in the composition ranges from between about 4% to about 6% (w/w) of the total composition. In an exemplary embodiment, the amount of antioxidant present in the composition is 5.3% (w/w).

It should be noted that the compositions of the present invention do not include crystallization inhibitors.

The composition of the present invention may further include inactive excipients that are added to the composition as a result of their incorporation into the individual active components. For instance, the fipronil component of the composition may be provided in a 95% solution, meaning that 95% of the fipronil component volume is active fipronil compound and the remaining 5% constitutes inactive excipients that are consequently introduced into the composition, as such the pesticide may not be 100% pure concentrate and may be purchased with other constituents. One skilled in the art will recognize that the inactive excipients include, but are not limited to binders, fillers, non-effervescent disintegrants, effervescent disintegrants, preservatives, diluents, lubricants, pH modifiers, stabilizers, and the like. It should, however, be understood that the inactive excipients are typically incorporated as a portion of the active ingredient components and comprise a small percentage (generally less than 1%) of the total composition volume, generally not affecting the physical characteristics of the composition.

It should be understood that the active components of the composition may be provided in the form of pure concentrate (100% concentration) or a diluted composition with additional excipients in the dosage form (i.e. the amount of active ingredient in the composition is less than or equal to 99.99%, and the remainder consists of inactive excipients). One of skill in the art will appreciate that the volume of active component added to the composition will need to be adjusted to account for the dilution and to ensure the end composition comprises the appropriate final concentration of each of the active components. One of skill in the art will also appreciate that the various components of the composition may be provided in a variety of dosage forms including, but not limited to a spot-on, powder, briquette, liquid solution or suspension, pellets, emulsion, aerosol, cream, gel, ointment, and the like. In a preferred embodiment, the composition of the present invention is prepared as a spot-on composition.

The basic composition of the present invention which can be used to prevent or reduce the incidence of flea allergy dermatitis in a companion animal by inhibiting blood feeding by ectoparasites generally includes cyphenothrin at a concentration ranging between about 1% and about 50% (w/w) and an organic solvent at a concentration ranging between about 50% and about 85% (w/w) of the total composition. In a preferred embodiment the present invention provides a method of reducing the incidence of flea allergy dermatitis, wherein the method comprises application of a composition comprising 20% (w/w) cyphenothrin to a companion animal. In another embodiment the present invention provides a method of reducing the incidence of flea allergy dermatitis, wherein the method comprises application of a composition comprising 30% (w/w) cyphenothrin, 2% (w/w) pyriproxyfen, and about 65% diethylene glycol monoethyl ether. In an additional embodiment the present invention provides a composition comprising 20% (w/w) cyphenothrin, 2% (w/w) pyriproxyfen and about 70% (w/w) diethylene glycol monoethyl ether.

Additionally, the pesticide composition of the current invention can be produced by contacting the various active components of the composition with one another to produce a formulation suitable for application to an animal's skin. It should be understood that the current invention encompasses a variety of physical formulations; however, the compositions of the current invention are generally directed to liquid solutions and suspensions. The formulations of the present invention may be prepared by standard techniques known in the art. For instance, in one embodiment where the desired formulation is a liquid solution, the composition is produced by bringing the cyphenothrin into contact with a solvent system and then gently heating and stirring the components until dissolved. In a preferred embodiment, the composition comprising cyphenothrin and a solvent system may further be contacted with an insect growth regulator, and the combination is then stirred to create a composition. A person having ordinary skill in the art will appreciate that the various components of the composition may be contacted and mixed with one another in any order desired, so long as the solution is adequately stirred and mixed.

The physical characteristics of the composition may vary depending upon the physical characteristics desired. However, the composition should be capable of application to the skin of an animal and provide adequate stasis to allow the active components of the topical composition to be absorbed by the host animal. Preferably, the compositions of the present invention have low viscosity. Viscosity is the measurement of flow resistance due to internal friction within the fluid, and is measured in centistokes (cSt). A lower cSt measurement means the fluid will flow with less resistance, because of minimal molecular friction within the fluid. The lower the viscosity the faster the fluid will flow. High viscosity substances are liquids that are thick and gelatinous in nature with slow flow. Low viscosity substances exhibit a fast flow with an example being water at room temperature (water at 20° C. has a viscosity of about 1 cSt; 1 cSt=1 $mm^2$/second). The compositions of the present invention typically have a viscosity ranging from about 0.01 $mm^2$/second to about 100 $mm^2$/second. In a more preferred embodiment, the composition has a viscosity ranging from about 1 $mm^2$/second to about 30 $mm^2$/second. In a further preferred embodiment, the composition has a viscosity ranging from about 4 $mm^2$/second to about 20 $mm^2$/second.

The composition of the present invention is intended to be administered topically to companion animals. The composition is preferably provided in the form of a liquid spot-on but can also be provided in the form of a shampoo, powder, spray, dip, gel, or any other form that allows topical administration to an animal. The invention contemplates that various other complimentary ingredients can be included in order to obtain the desired form.

(b) Application

In one embodiment, the method of inhibiting blood feeding and killing ectoparasites is carried out such that the composition is applied as a spot-on composition to a companion animal in a volume sufficient to deliver a dosage of cyphenothrin ranging from about 0.1 mg/kg to about 40 mg/kg of host animal body weight. In a preferred embodiment, the dose of cyphenothrin administered to the animal ranges from about 0.5 mg/kg to about 20 mg/kg of host animal body weight. In a more preferred embodiment, the composition application comprises a volume sufficient to deliver a cyphenothrin dose ranging from about 0.5 mg/kg to about 10 mg/kg of host animal body weight.

One of skill in the art will understand that the dosage ranges provided above are approximate values that may vary within a broad range. The variance in dose is due to the fact that, in practice, the spot-on composition will be administered in defined doses and volumes to animals within a certain range of weights (e.g., 6.0 mL for dogs weighing over 61 pounds, 4.5 mL for dogs weighing 40 to 60 pounds, and 3.0 mL for dogs weighing 21 to 39 pounds). As a result, the dosage actually applied to the animal may vary by a factor ranging from 0.1 to 10 relative to the preferred dose, without imparting any additional risks pertaining to toxicity or decreased efficacy.

Although the components of the composition are effective against a wide variety of ectoparasites, the composition is especially developed for the treatment of fleas (including the *Ctenocephalides* species) and ticks (the *Rhipecephalus*, *Ixodes*, and *Trichodectes* species). Furthermore, the frequency of application may be varied according to the needs of the individual animal, as well as the severity of infestation. The treatment of ectoparasites may be repeated as often as once weekly, or may be reserved for one-time acute treatments of infestations or flare-ups. In one embodiment of the current invention, the treatment of fleas may be repeated about every four weeks, five weeks, or six weeks. In another embodiment, the spot-on composition is applied to the host animal for a one-time treatment of the pest infestation. With regard to the treatment of ticks, the application schedule for the spot-on composition will vary depending on the type of tick being treated. It is generally recommended that treatment of paralytic ticks (*Ixodes* species) occur more frequently than other species. In an embodiment of the current invention, paralytic ticks are treated at a frequency ranging from one to four weeks, with treatment every two weeks being preferred. Other genera of ticks generally have a treatment schedule similar to treatment of flea infestation, preferably ranging from approximately four to six weeks.

(c) Methods of the Invention

The compositions and methods according to this invention are intended for application to animals, in particular domestic or companion animals such as dogs and cats, and are generally applied by deposition directly onto the skin (e.g., "spot-on" or "pour-on" application, spray application, shampoo application, etc.).

In a preferred embodiment, the methods for reducing the incidence of flea allergy dermatitis comprise administering a localized cutaneous application between the shoulders of the animal, of a spot-on composition as described. Treatment typically comprises a localized application over a surface area of less than 10 cm$^2$, especially of between 5 and 10 cm$^2$. Generally, the spot-on composition should be applied to an area where the animal cannot lick the application area, as licking of the application area may lead to transient adverse effects, such as excessive salivation. In particular, application is preferred at two points and preferably localized between the animal's shoulders. After the spot-on composition has been applied, the composition diffuses, in particular over the animal's entire body, and then dries without crystallizing or modifying the appearance (in particular absence of any whitish deposit or dusty appearance) or the feel of the animal's fur. Further, the method of the current invention is preferably directed to application of the spot-on composition to the skin of the animal once every four weeks to ensure continuous treatment and prevention of pest infestation. Typically, the active constituents are applied to the host animal together in a single formulation.

In a specific embodiment, the method for reducing the incidence of flea allergy dermatitis in a dog weighing between 11 and 20 pounds by reducing blood feeding by ectoparasites on the dog by at least 80% comprises the steps of: removing one 4.0 mL tube containing a composition comprising about 30% (w/w) cyphenothrin, about 2% (w/w) pyriproxyfen, and about 68% (w/w) diethylene glycol monoethyl ether from product packaging; holding the tube upright with the dispensing end pointing up; cutting or tearing the dispensing end of the tube; holding the dog in place with one hand; inverting the tube such that the dispensing end is pointing at the dog's back; parting the dog's hair with the dispensing end of the tube to reveal the skin of the dog; squeezing the tube to apply the composition to the skin of the dog; holding the dog for between 5 and 10 seconds to ensure the contents have been absorbed into the dog's skin; disposing of the tube in a trash receptacle; and repeating the application once every four weeks. Preferably, the step of squeezing the tube to apply the composition to the dog further comprises applying a portion of the contents of the tube to a starting location high on the back of the dog's neck and squeezing the tube firmly while depositing the remaining contents of the tube in a line from the starting location to an ending point midway between the dog's neck and tail.

In another specific embodiment, the method for reducing the incidence of flea allergy dermatitis in a dog weighing between 21 and 39 pounds by reducing blood feeding by ectoparasites on the dog by at least 80% comprises the steps of: removing one 3.0 mL tube containing a composition comprising about 30% (w/w) cyphenothrin, about 2% (w/w) pyriproxyfen, and about 68% (w/w) diethylene glycol monoethyl ether from product packaging; holding the tube upright with the dispensing end pointing up; cutting or tearing the dispensing end of the tube to open the tube; holding the dog in place with one hand; inverting the tube such that the dispensing end is pointing at the dog's back; parting the dog's hair with the dispensing end of the tube to reveal the skin of the dog; squeezing the tube to apply the composition to the skin of the dog; holding the dog for between 5 and 10 seconds to ensure the contents have been absorbed into the dog's skin; disposing of the tube in a trash receptacle; and repeating the application once every four weeks. Preferably, the step of squeezing the tube to apply the composition to the dog further comprises applying a portion of the contents of the tube to a starting location high on the back of the dog's neck and squeezing the tube firmly while depositing the remaining contents of the tube in a line from the starting location to an ending point midway between the dog's neck and tail.

In yet another specific embodiment, the method for reducing the incidence of flea allergy dermatitis in a dog weighing between 40 and 60 pounds by reducing blood feeding by ectoparasites on the dog by at least 80% comprises the steps of: removing one 4.5 mL tube containing a composition comprising about 30% (w/w) cyphenothrin, about 2% (w/w) pyriproxyfen, and about 68% (w/w) diethylene glycol monoethyl ether from product packaging; holding the tube upright with the dispensing end pointing up; cutting or tearing the dispensing end of the tube to open the tube; holding the dog in place with one hand; inverting the tube such that the dispensing end is pointing at the dog's back; parting the dog's hair with the dispensing end of the tube to reveal the skin of the dog; squeezing the tube to apply the composition to the skin of the dog; holding the dog for between 5 and 10 seconds to ensure the contents have been absorbed into the dog's skin; disposing of the tube in a trash receptacle; and repeating the application once every four weeks. Preferably, the step of squeezing the tube to apply the composition to the dog further comprises applying a portion of the contents of the tube to a starting location high on the back of the dog's neck and squeezing the tube firmly while depositing the remaining contents of the tube in a line from the starting location to an ending point midway between the dog's neck and tail.

In a further specific embodiment, the method for reducing the incidence of flea allergy dermatitis in a dog weighing at least 61 pounds by reducing blood feeding by ectoparasites on the dog by at least 80% comprises the steps of: removing one 6.0 mL tube containing a composition comprising about 30% (w/w) cyphenothrin, about 2% (w/w) pyriproxyfen, and about 68% (w/w) diethylene glycol monoethyl ether from product packaging; holding the tube upright with the dispensing end pointing up; cutting or tearing the dispensing end of the tube to open the tube; holding the dog in place with one hand; inverting the tube such that the dispensing end is pointing at the dog's back; parting the dog's hair with the dispensing end of the tube to reveal the skin of the dog; squeezing the tube to apply the composition to the skin of the dog; holding the dog for between 5 and 10 seconds to ensure the contents have been absorbed into the dog's skin; disposing of the tube in a trash receptacle; and repeating the application once every four weeks. Preferably, the step of squeezing the tube to apply the composition to the dog further comprises applying a portion of the contents of the tube to a starting location high on the back of the dog's neck and squeezing the tube firmly while depositing the remaining contents of the tube in a line from the starting location to an ending point midway between the dog's neck and tail.

The current invention embodies methods of preventing or reducing the incidence of flea allergy dermatitis in a companion animal. The methods comprise inhibiting blood feeding by ectoparasites on a companion animal. In preferred embodiments, the methods comprise inhibiting blood feeding by fleas on a companion animal.

As described in the examples, reduction in blood feeding may be determined by calculating the percentage of each animal's killed and repelled fleas containing blood. In some embodiments, blood feeding by ectoparasites on the companion animal is reduced by at least 50, 55, 60, 65, 70, 75, 80, 85, 90, 95 or 100% through the methods of the invention. In other embodiments, at least 75, 80, 85, 90, 95 or 100% reduction in blood feeding by ectoparasites is achieved by the methods of the invention. In preferred embodiments, at least 80% reduction in blood feeding by ectoparasites is achieved by the methods of the invention. In other preferred embodiments, at least 90% reduction in blood feeding by ectoparasites is achieved by the methods of the invention.

Although the invention described herein is susceptible to various modifications and alternative iterations, specific embodiments thereof have been described in greater detail above. It should be understood, however, that the detailed description of the composition is not intended to limit the invention to the specific embodiments disclosed. Rather, it should be understood that the invention is intended to cover all modifications, equivalents, and alternatives falling within the spirit and scope of the invention as defined by the claim language.

DEFINITIONS

As used herein, the terms "to reduce the incidence of flea allergy dermatitis" and "decrease the incidence of flea allergy dermatitis" mean lowering the rate of occurrence of flea allergy dermatitis induced by flea biting in animals who are administered a composition comprising up to about 50% (w/w) cyphenothrin according to the methods of the present invention relative to the rate of occurrence of flea allergy dermatitis in animals who are not administered the same or similar composition.

As used herein, the terms "about" and "approximately" designate that a value is within a statistically meaningful range. Such a range can be typically within 20%, more typically still within 10%, and even more typically within 5% of a given value or range. The allowable variation encompassed by the terms "about" and "approximately" depends on the particular system under study and can be readily appreciated by one of ordinary skill in the art.

As used herein, the term "w/w" designates the phrase "by weight and is used to describe the concentration of a particular substance in a mixture or solution.

As used herein, the term "mL/kg" designates milliliters of composition per kilogram of body weight.

As used herein, the term "treatment" or "treating" of a condition, such as pest infestation, includes inhibiting an existing condition or arresting its development; or ameliorating or causing regression of the condition. The term "preventing" or "prevention" of a condition, such as insect or pest infestation, includes substantially blocking or inhibiting the development or growth of a condition before it starts. Compositions that treat or prevent infestations herein will preferably exhibit at least 90% efficacy.

As used herein, the term "pesticide" or "pesticidal" refers to an agent or a composition comprising an agent that is capable of preventing, reducing or eliminating pest infestations. Preferred pesticides of the present invention include fipronil, cyphenothrin, and etofenprox.

As used herein, the term "insect growth regulator" or "IGR" refers to an agent that is capable of interrupting or inhibiting the life cycle of a pest such that the pest never matures into an adult and becomes incapable of reproducing. A preferred IGR of the present invention is pyriproxyfen.

As used herein, the terms "companion animal" or "animal" refer to an animal typically kept as a pet for keeping in the vicinity of a home or domestic environment regardless of whether the animal is kept indoors or outdoors. Specific examples of companion animals include but are not limited to dogs, cats, rabbits, ferrets, horses, and hamsters.

As used herein, the term "ectoparasite" refers to any parasite that lives on the outside of an animal's body, including but not limited to fleas, ticks, louse flies, keds, mosquitoes, and mites.

The following examples are intended to further illustrate and explain the present invention. The invention, therefore, should not be limited to any of the details in these examples.

EXAMPLES

Example 1

Method of Making a Cyphenothrin/IGR Spot-on Composition for Dogs

| Ingredient | Concentration |
| --- | --- |
| Cyphenothrin | 20% |
| Pyriproxyfen | 2% |
| Diethylene glycol monoethyl ether | 78% |

The diethylene glycol monoethyl ether was charged to a vessel and heated to a temperature of 50° C. (about 1 hour). One heated, the cyphenothrin and pyriproxyfen were charged to the vessel and all components were mixed until a homogenous solution was formed (about 1 hour).

Example 2

Efficacy Evaluation of a Spot-on Composition Containing Fipronil and Cyphenothrin, Compared to Other Spot-on Compositions Against Fleas (*Ctenocephalides Felis*) and Ticks (*Rhipicephalus sanguineus* and *Dermacentor variabilis*) on Dogs A cyphenothrin-fortified test substance containing 8.2% cyphenothrin and 9.8% fipronil was compared for efficacy to (1) a spot-on composition containing 5.2% cyphenothrin and 9.8% fipronil, (2) a spot-on composition containing 9.8% fipronil and 8.8% S-methoprene, (3) a spot-on composition containing 8.8% imidacloprid, 44% permethrin, and 0.44% pyriproxyfen, and (4) a spot-on composition containing 6.4% fipronil, 7.6% amitraz and 5.8% methoprene. Each of the compositions, applied once, was evaluated for efficacy against pre-existing infestations of fleas and ticks and against weekly re-infestations with new fleas and ticks over a period of 37 days. Flea and tick counts on the dogs and tray counts of repelled/killed fleas and ticks were performed at 1, 4 and 6 hours after treatment and after each re-infestation to compare speed of kill of the test substances. On-animal flea and tick counts were also performed at 24 and 48 hours after treatment and after each re-infestation. The re-infesting tick species were alternated between *Dermacentor variabilis* and *R. sanguineus*. The residual efficacy data against new fleas and tick for all five test substances met or exceeded the 90% threshold value required to support efficacy of one month. Furthermore, their efficacy (except for ticks on dogs treated with the composition containing 9.8% fipronil and 8.8% S-methoprene) exceeded one month by an additional week.

Treatment Grouping and Infestation Schedule.

Dogs weighing between 17 and 42 lb were allocated to 6 groups so that their mean group weights were close to the mid-point of their respective weight classes. An excess of test subjects was pre-tested for their ability to host fleas and ticks and the least suitable subjects were removed from the study to leave the required 42 subjects.

Table 1 outlines the grouping of dogs and their administered treatment. Group A dogs were untreated controls. The spot-on composition containing 9.8% fipronil and 8.2% cyphenothrin was applied to the 6 dogs of Group B. The spot-on composition containing 9.8% fipronil and 5.2% cyphenothrin was applied to the 6 dogs in Group C. The spot-on composition containing 9.8% fipronil and 8.2% methoprene, purchased at retail, was applied to the 6 dogs in Group D. The spot-on composition containing 8.8% imidacloprid, 44% permethrin and 0.44% pyriproxyfen, purchased at retail, was applied to the 6 dogs in group E. The spot-on composition containing 6.4% fipronil, 7.6% amitraz and 5.8% methoprene, purchased at retail, was applied to the 6 dogs in Group F. The unit dose volumes for the dogs in Groups C, D, E and F were applied from the commercial pipettes, in accordance with their label instructions for dogs in their respective weight classes. The unit dose volume of the spot-on composition prepared in accordance with the current invention was drawn from a bulk preparation and applied at the same unit dose volume (1.34 mL) as the composition containing 9.8% fipronil and 5.2% cyphenothrin for that weight class.

TABLE 1

Grouping and Treatment

| Group | Weight | Treatment |
| --- | --- | --- |
| A | 17 lb-42 lb | None |
| B | 17 lb-42 lb | 9.8% fipronil/8.2% cyphenothrin |
| C | 17 lb-42 lb | 9.8% fipronil/5.2% cyphenothrin |
| D | 17 lb-42 lb | 9.8% fipronil/8.2% methoprene |
| E | 17 lb-42 lb | 8.8% imidacloprid/44% permethrin/ 0.44% pyriproxyfen |
| F | 17 lb-42 lb | 6.4% fipronil/7.6% amitraz/5.8% methoprene |

The dogs were infested with 100 fleas and 50 ticks on days −1, 8, 14, 21, 28 and 35. Flea specie was the cat flea *Ctenocephalides felis* and tick species were *Rhipicephalus sanguineus* and *Dermacentor variabilis*, applied on alternate successive weeks.

Before each infestation/re-infestation and for 6 hours thereafter, the dogs were held in metal cages with a sheet of white paper in the soil tray to collect and enable counting of repelled and killed parasites at 1, 4 and 6 hours. Hand counts were performed at these times without removing or damaging the parasites. Fleas and tick hand counts were also conducted at 24 hours and comb counts, removing and destroying all parasites, were conducted at 48 hours. Only the groups of dogs treated with the spot-on composition of the present invention, the composition containing 9.8% fipronil and 5.2% cyphenothrin, and the composition containing 6.4% fipronil, 7.6% amitraz and 5.8% methoprene were subject to the 6 hour tray collection procedure.

Fleas on the catch trays at 1 hour after each successive re-infestation were tested to determine if they had been able to feed on the dogs before being killed or repelled. 10 fleas, selected randomly, or whatever numbers were present if less than 10, were squashed in situ on the white paper tray liner and observed for red staining. Since few fleas dropped off the control dogs, an attempt was made to test the control fleas combed off at 48 hours proved futile since these fleas' bodies were so hard and darkened that this procedure was not successful.

Efficacy Against Fleas and Ticks.

Efficacy against fleas and ticks was calculated at each time point using two different formulae.

Efficacy #1 is the formula used by most the registrants since the facilities, effort and costs of collecting and counting repelled parasites from animals confined in metabolism cages is substantial. This formula calculates the reduction in parasite burden for each treated dog, compared with and expressed as percent of the mean control group burden, without reference to the numbers of repelled and killed fleas, as follows:

$$\frac{\text{Mean number of live fleas/ticks on untreated dogs} - \text{Number of live fleas/ticks on each treated dog} \times 100}{\text{Mean number of live fleas/ticks on untreated dogs}}$$

Efficacy #2 first calculates the numbers of parasites repelled from each dog as a percent of the total parasite burden for that dog, derived by the addition of remaining live parasites and accumulated dead/repelled parasites, as follows:

$$\frac{\text{Number of killed/repelled fleas/ticks on liner below each treated dog} \times 100}{\text{Number of fleas/ticks on that dog} + \text{number of killed/repelled fleas/ticks}}.$$

The formula for efficacy #2 does not, however, take into consideration the numbers of parasites that, for unknown reasons unrelated to any treatment, will progressively fall off the dog and/or die and therefore negates the value of having untreated control dogs. In order to adjust for this "normal" parasite attrition, tray counts for repelled/killed parasites are also conducted for each untreated control with individual "efficacy" values derived as above. The mean group efficacy value (Eff#2) for treatment is adjusted/reduced by the contemporaneous "normal control attrition efficacy" to provide controlled group mean efficacy values attributable to only treatment, as follows:

Group mean percent value of $$\frac{[\text{Number of killed/repelled fleas/ticks on liner below each treated dog} \times 100}{\text{Number of fleas/ticks on that dog} + \text{number of killed/repelled fleas/ticks}\}$$

Minus group mean percent value of $$\frac{[\text{Number of killed/repelled fleas/ticks on liner below each control dog} \times 100}{\text{Number of live fleas/ticks on that dog} + \text{number of killed/repelled fleas/ticks}]$$

Efficacy in Preventing Fleas Biting and Feeding

Efficacy in preventing fleas biting and feeding on each treated dog was calculated as follows:

Number of fleas from that dog with blood−number of fleas from that dog squashed×100

Mean group efficacy values (+/− standard deviation) were calculated from the aggregate individual percentage efficacy values. Group efficacy (mean+/− standard deviation) values are summarized in Tables 2-12.

TABLE 2

Summary Mean Group Efficacies against Fleas and Ticks (Day 0)

| Group | Days Test | | −1 | 0 | @ 1 hour* % effic | @ 4 hours* % effic | @ 6 hours* % effic | 1 * % effic | 2 % effic |
|---|---|---|---|---|---|---|---|---|---|
| B 8.2% | Fleas | Eff #1 | I | T | 56% | 91% | 100% | 100% | 100% |
|  |  | Eff #2 | N | R | 31% | 95% | 100% |  |  |
|  | Ticks | Eff #1 | F | E | 65% | 73% | 91% | 98% | 99% |
|  |  | Eff #2 | E | A | 46% | 69% | 89% |  |  |
| C 5.2% | Fleas | Eff #1 | S | T | 60% | 76% | 81% | 100% | 100% |
|  |  | Eff #2 | T |  | 43% | 84% | 91% |  |  |
|  | Ticks | Eff #1 |  |  | 48% | 72% | 79% | 90% | 97% |
|  |  | Eff #2 |  |  | 30% | 61% | 75% |  |  |
| D Fl+ | Fleas | Eff #1 |  |  | 58% | 74% |  | 100% | 100% |
|  |  | Eff #2 |  |  | 3% | 63% |  |  |  |
|  | Ticks | Eff #1 |  |  | 45% | 53% |  | 92% | 99% |
|  |  | Eff #2 |  |  | 7% | 24% |  |  |  |
| E Advantix+ | Fleas | Eff #1 |  |  | 68% | 93% |  | 100% | 100% |
|  |  | Eff #2 |  |  | 22% | 91% |  |  |  |
|  | Ticks | Eff #1 |  |  | 11% | 53% |  | 66% | 73% |
|  |  | Eff #2 |  |  | 11% | 36% |  |  |  |
| F Certifect | Fleas | Eff #1 |  |  | 64% | 75% | 79% | 100% | 100% |
|  |  | Eff #2 |  |  | 14% | 50% | 69% |  |  |
|  | Ticks | Eff #1 |  |  | 16% | 59% | 83% | 87% | 96% |
|  |  | Eff #2 |  |  | 16% | 72% | 86% |  |  |

1 Efficacy formula is (mean parasites on controls − parasites on treated dog)/(mean control parasite count) %, independent of tray counts of repelled/killed parasites
2 efficacy formula includes adjustment for number of parasites in tray counts, adjusted for tray counts of controls

TABLE 3

Summary Mean Group Efficacies against Fleas and Ticks (Week 1)

| Days Group | Test | | 8 | @ 1 hour* % effic | @ 4 hours* % effic | @ 6 hours* % effic | 9 * % effic | 10 % effic |
|---|---|---|---|---|---|---|---|---|
| B 8.2% | Fleas | Eff #1 | I | 66% | 99% | 100% | 100% | 100% |
|  |  | Eff #2 | N | 66% | 99% | 100% |  |  |
|  | Ticks | Eff #1 | F | 88% | 88% | 93% | 100% | 100% |
|  |  | Eff #2 | E | 74% | 75% | 78% |  |  |
| C 5.2% | Fleas | Eff #1 | S | 85% | 95% | 100% | 100% | 100% |
|  |  | Eff #2 | T | 78% | 97% | 100% |  |  |
|  | Ticks | Eff #1 |  | 74% | 78% | 82% | 100% | 100% |
|  |  | Eff #2 |  | 56% | 67% | 70% |  |  |
| D Fl+ | Fleas | Eff #1 |  | 37% | 91% |  | 100% | 100% |
|  |  | Eff #2 |  | 16% | 94% |  |  |  |

TABLE 3-continued

Summary Mean Group Efficacies against Fleas and Ticks (Week 1)

| Days Group | Test | | 8 | @ 1 hour* % effic | @ 4 hours* % effic | @ 6 hours* % effic | 9 * % effic | 10 % effic |
|---|---|---|---|---|---|---|---|---|
| | Ticks | Eff #1 | | 29% | 48% | | 100% | 100% |
| | | Eff #2 | | 12% | 41% | | | |
| E Advantix+ | Fleas | Eff #1 | | 93% | 98% | | 100% | 100% |
| | | Eff #2 | | 79% | 98% | | | |
| | Ticks | Eff #1 | | 94% | 96% | | 100% | 100% |
| | | Eff #2 | | 88% | 81% | | | |
| F Certifect | Fleas | Eff #1 | | 70% | 93% | 98% | 100% | 100% |
| | | Eff #2 | | 50% | 95% | 98% | | |
| | Ticks | Eff #1 | | 59% | 97% | 100% | 100% | 100% |
| | | Eff #2 | | 26% | 83% | 86% | | |

1 Efficacy formula is (mean parasites on controls − parasites on treated dog)/(mean control parasite count) %, independent of tray counts of repelled/killed parasites
2 efficacy formula includes adjustment for number of parasites in tray counts, adjusted for tray counts of controls

TABLE 4

Summary Mean Group Efficacies against Fleas and Ticks (Week 2)

| Days Group | Test | | 14 | @ 1 hour* % effic | @ 4 hours* % effic | @ 6 hours* % effic | 15 * % effic | 16 % effic |
|---|---|---|---|---|---|---|---|---|
| B 8.2% | Fleas | Eff #1 | I | 63% | 84% | 98% | 100% | 100% |
| | | Eff #2 | N | 72% | 92% | 99% | | |
| | Ticks | Eff #1 | F | 94% | 100% | 100% | 100% | 100% |
| | | Eff #2 | E | 100% | 73% | 73% | | |
| C 5.2% | Fleas | Eff #1 | S | 28% | 86% | 100% | 100% | 100% |
| | | Eff #2 | T | 67% | 93% | 100% | | |
| | Ticks | Eff #1 | | 79% | 83% | 57% | 100% | 100% |
| | | Eff #2 | | 54% | 53% | 57% | | |
| D Fl+ | Fleas | Eff #1 | | 40% | 85% | | 100% | 100% |
| | | Eff #2 | | 62% | 88% | | | |
| | Ticks | Eff #1 | | 53% | 40% | | 92% | 98% |
| | | Eff #2 | | 2% | −4% | | | |
| E Advantix+ | Fleas | Eff #1 | | 78% | 96% | | 100% | 100% |
| | | Eff #2 | | 88% | 98% | | | |
| | Ticks | Eff #1 | | 83% | 85% | | 100% | 100% |
| | | Eff #2 | | 72% | 70% | | | |
| F Certifect | Fleas | Eff #1 | | 35% | 90% | 93% | 100% | 100% |
| | | Eff #2 | | 56% | 95% | 97% | | |
| | Ticks | Eff #1 | | 37% | 91% | 100% | 100% | 100% |
| | | Eff #2 | | 49% | 71% | 73% | | |

1 Efficacy formula is (mean parasites on controls − parasites on treated dog)/(mean control
2 efficacy formula includes adjustment for number of parasites in tray counts, adjusted for

TABLE 5

Summary Mean Group Efficacies against Fleas and Ticks (Week 3)

| Days Group | Test | | 21 | @ 1 hour* % effic | @ 4 hours* % effic | @ 6 hours* % effic | 22 * % effic | 23 % effic |
|---|---|---|---|---|---|---|---|---|
| B 8.2% | Fleas | Eff #1 | I | 30% | 82% | 95% | 100% | 100% |
| | | Eff #2 | N | 34% | 83% | 95% | | |
| | Ticks | Eff #1 | F | 59% | 85% | 91% | 100% | 100% |
| | | Eff #2 | E | 42% | 61% | 69% | | |
| C 5.2% | Fleas | Eff #1 | S | 33% | 80% | 94% | 100% | 100% |
| | | Eff #2 | T | 23% | 77% | 93% | | |
| | Ticks | Eff #1 | | 48% | 83% | 90% | 100% | 100% |
| | | Eff #2 | | 22% | 56% | 93% | | |
| D Fl+ | Fleas | Eff #1 | | 21% | 58% | | 100% | 100% |
| | | Eff #2 | | 4% | 40% | | | |
| | Ticks | Eff #1 | | 30% | 49% | | 94% | 99% |
| | | Eff #2 | | 9% | 25% | | | |
| E Advantix+ | Fleas | Eff #1 | | 58% | 84% | | 100% | 100% |
| | | Eff #2 | | 67% | 87% | | | |
| | Ticks | Eff #1 | | 52% | 84% | | 100% | 100% |

TABLE 5-continued

Summary Mean Group Efficacies against Fleas and Ticks (Week 3)

| Days Group | Test | | 21 % effic | @ 1 hour* % effic | @ 4 hours* % effic | @ 6 hours* % effic | 22 * % effic | 23 % effic |
|---|---|---|---|---|---|---|---|---|
| F Certifect | Fleas | Eff #1 | | 29% | 84% | 89% | 100% | 100% |
| | | Eff #2 | | 17% | 76% | 86% | | |
| | Ticks | Eff #1 | | 28% | 66% | 81% | 100% | 100% |
| | | Eff #2 | | 20% | 39% | 58% | | |

1 Efficacy formula is (mean parasites on controls − parasites on treated dog)/(mean control parasite count) %, independent of tray counts of repelled/killed parasites
2 efficacy formula includes adjustment for number of parasites in tray counts, adjusted for tray counts of controls

TABLE 6

Summary Mean Group Efficacies against Fleas and Ticks (Week 4)

| Days Group | Test | | | 28 % effic | @ 1 hour* % effic | @ 4 hours* % effic | @ 6 hours* % effic | 29 * % effic | 30 % effic |
|---|---|---|---|---|---|---|---|---|---|
| B 8.2% | Fleas | Eff #1 | I | | 23% | 51% | 82% | 100% | 100% |
| | | Eff #2 | N | | 20% | 47% | 80% | | |
| | Ticks | Eff #1 | F | | 66% | 78% | 88% | 100% | 99% |
| | | Eff #2 | E | | 63% | 75% | 85% | | |
| C 5.2% | Fleas | Eff #1 | S | | 12% | 67% | 84% | 100% | 100% |
| | | Eff #2 | T | | 11% | 62% | 80% | | |
| | Ticks | Eff #1 | | | 56% | 76% | 89% | 100% | 100% |
| | | Eff #2 | | | 61% | 76% | 89% | | |
| D Fl+ | Fleas | Eff #1 | | | 6% | 51% | | 98% | 100% |
| | | Eff #2 | | | 4% | 51% | | | |
| | Ticks | Eff #1 | | | 7% | 47% | | 77% | 93% |
| | | Eff #2 | | | 19% | 49% | | | |
| E Advantix+ | Fleas | Eff #1 | | | 55% | 64% | | 94% | 99% |
| | | Eff #2 | | | 61% | 67% | | | |
| | Ticks | Eff #1 | | | 64% | 47% | | 95% | 98% |
| | | Eff #2 | | | 70% | 63% | | | |
| F Certifect | Fleas | Eff #1 | | | 33% | 69% | 79% | 100% | 100% |
| | | Eff #2 | | | 3% | 53% | 71% | | |
| | Ticks | Eff #1 | | | 2% | 55% | 78% | 99% | 100% |
| | | Eff #2 | | | 13% | 59% | 78% | | |

1 Efficacy formula is (mean parasites on controls − parasites on treated dog)/(mean control parasite count) %, independent of tray counts of repelled/killed parasites
2 efficacy formula includes adjustment for number of parasites in tray counts, adjusted for tray counts of controls

TABLE 7

Summary Mean Group Efficacies against Fleas and Ticks (Week 5)

| Days Group | Test | | | 37 % effic | @ 1 hour* % effic | @ 4 hours* % effic | @ 6 hours* % effic | 36 * % effic | 37 % effic |
|---|---|---|---|---|---|---|---|---|---|
| B 8.2% | Fleas | Eff #1 | I | | 56% | 73% | 79% | 100% | 100% |
| | | Eff #2 | N | | 35% | 64% | 71% | | |
| | Ticks | Eff #1 | F | | 40% | 59% | 71% | 97% | 100% |
| | | Eff #2 | E | | 45% | 54% | 69% | | |
| C 5.2% | Fleas | Eff #1 | S | | 63% | 82% | 79% | 100% | 100% |
| | | Eff #2 | T | | 35% | 68% | 77% | | |
| | Ticks | Eff #1 | | | 29% | 58% | 72% | 98% | 100% |
| | | Eff #2 | | | 31% | 54% | 68% | | |
| D Fl+ | Fleas | Eff #1 | | | 45% | 61% | | 99% | 100% |
| | | Eff #2 | | | 12% | 42% | | | |
| | Ticks | Eff #1 | | | −6% | 22% | | 69% | 84% |
| | | Eff #2 | | | 13% | 24% | | | |
| E Advantix+ | Fleas | Eff #1 | | | 64% | 81% | | 99% | 99% |
| | | Eff #2 | | | 57% | 74% | | | |
| | Ticks | Eff #1 | | | 50% | 76% | | 96% | 99% |
| | | Eff #2 | | | 63% | 81% | | | |
| F Certifect | Fleas | Eff #1 | | | 60% | 73% | 64% | 99% | 99% |
| | | Eff #2 | | | 11% | 45% | 45% | | |
| | Ticks | Eff #1 | | | 11% | 42% | 50% | 97% | 99% |
| | | Eff #2 | | | 18% | 43% | 48% | | |

1 Efficacy formula is (mean parasites on controls − parasites on treated dog)/(mean control parasite count) %, independent of tray counts of repelled/killed parasites
2 efficacy formula includes adjustment for number of parasites in tray counts, adjusted for tray counts of controls

TABLE 8

Blood feeding counts on repelled/dead fleas (Week 1)

| Dog no | Group | Day of Study 0 | 8 | Paper | No tested | no positive | % positive |
|---|---|---|---|---|---|---|---|
| | | | 8 − 1 h | | | | |
| 449 | B | T | I | 17 | 10 | 4 | 40% |
| 368 | B | R | N | 15 | 10 | 3 | 30% |
| 507 | B | E | F | 14 | 10 | 2 | 20% |
| 483 | B | A | E | 12 | 10 | 3 | 30% |
| 515 | B | T | S | 15 | 10 | 2 | 20% |
| 490 | B | | T | 13 | 10 | 2 | 20% |
| Mean | | | | 14.3 | | 2.7 | 27% |
| +/−s.d. | | | | 1.8 | | 0.8 | 8% |
| 512 | C | T | I | 8 | 8 | 2 | 25% |
| 421 | C | R | N | 18 | 10 | 3 | 30% |
| 234 | C | E | F | 11 | 10 | 2 | 20% |
| 425 | C | A | E | 17 | 10 | 3 | 30% |
| 513 | C | T | S | 12 | 10 | 4 | 40% |
| 312 | C | | T | 18 | 10 | 1 | 10% |
| Mean | | | | 14.0 | | 2.5 | 26% |
| +/−s.d. | | | | 4.2 | | 1.0 | 10% |
| 416 | D | T | I | 0 | 0 | 0 | |
| 517 | D | R | N | 2 | 2 | 2 | 100% |
| 470 | D | E | F | 4 | 4 | 4 | 100% |
| 518 | D | A | E | 0 | 0 | 0 | |
| 380 | D | T | S | 9 | 4 | 3 | 75% |
| 504 | D | | T | 14 | 10 | 8 | 80% |
| Mean | | | | 4.8 | | 2.8 | 89% |
| +/−s.d. | | | | 5.6 | | 3.0 | 13% |
| 429 | E | T | I | 0 | 0 | 0 | |
| 412 | E | R | N | 20 | 10 | 6 | 60% |
| 411 | E | E | F | 19 | 10 | 7 | 70% |
| 419 | E | A | E | 22 | 10 | 10 | 100% |
| 378 | E | T | S | 33 | 10 | 7 | 70% |
| 523 | E | | T | 29 | 10 | 8 | 80% |
| Mean | | | | 20.5 | | 6.3 | 76% |
| +/−s.d. | | | | 11.4 | | 3.4 | 15% |
| 517 | F | T | I | 7 | 7 | 6 | 86% |
| 381 | F | R | N | 4 | 4 | 4 | 100% |
| 232 | F | E | F | 6 | 6 | 5 | 83% |
| 427 | F | A | E | 12 | 10 | 8 | 80% |
| 481 | F | T | S | 8 | 8 | 8 | 100% |
| 462 | F | | T | 11 | 10 | 9 | 90% |
| Mean | | | | 8.0 | | 6.7 | 90% |
| +/−s.d. | | | | 3.0 | | 2.0 | 9% |

TABLE 9

Blood feeding counts on repelled/dead fleas (Week 2)

| Dog no | Group | Day of Study 14 | Paper | No tested | no positive | % positive |
|---|---|---|---|---|---|---|
| | | 14 + 1 h | | | | |
| 449 | B | I | 22 | 10 | 1 | 10% |
| 368 | B | N | 37 | 10 | 0 | 0% |
| 507 | B | F | 47 | 10 | 0 | 0% |
| 483 | B | E | 38 | 10 | 0 | 0% |
| 515 | B | S | 41 | 10 | 1 | 10% |
| 490 | B | T | 45 | 10 | 0 | 0% |
| Mean | | | 38.3 | | | 3% |
| +/−s.d. | | | 8.9 | | | 5% |
| 512 | C | I | 25 | 10 | 1 | 10% |
| 421 | C | N | 49 | 10 | 2 | 20% |
| 234 | C | F | 46 | 10 | 0 | 0% |
| 425 | C | E | 44 | 10 | 0 | 0% |
| 513 | C | S | 43 | 10 | 3 | 30% |
| 312 | C | T | 51 | 10 | 0 | 0% |
| Mean | | | 22 | | | 10% |
| +/−s.d. | | | 9.3 | | | 13% |
| 416 | D | I | 39 | 9 | 2 | 22% |
| 517 | D | N | 51 | 10 | 0 | 0% |
| 470 | D | F | 36 | 10 | 1 | 10% |
| 518 | D | E | 36 | 10 | 2 | 20% |
| 380 | D | S | 47 | 10 | 4 | 40% |
| 504 | D | T | 47 | 10 | 3 | 30% |
| Mean | | | 42.7 | | | 20% |
| +/−s.d. | | | 6.5 | | | 14% |
| 429 | E | I | 0 | 10 | 8 | 80% |
| 412 | E | N | 20 | 10 | 7 | 70% |
| 411 | E | F | 23 | 10 | 5 | 50% |
| 419 | E | E | 24 | 10 | 9 | 90% |
| 378 | E | S | 33 | 10 | 8 | 80% |
| 523 | E | T | 32 | 10 | 6 | 60% |
| Mean | | | 22.0 | | | 72% |
| +/−s.d. | | | 11.9 | | | 15% |
| 517 | F | I | 31 | 7 | 4 | 57% |
| 381 | F | N | 31 | 10 | 5 | 50% |
| 232 | F | F | 27 | 10 | 4 | 40% |
| 427 | F | E | 20 | 10 | 8 | 80% |
| 481 | F | S | 20 | 10 | 6 | 60% |
| 462 | F | T | 20 | 10 | 5 | 50% |
| Mean | | | 24.8 | | 5.3 | 56% |
| +/−s.d. | | | 5.5 | | 1.5 | 14% |

TABLE 10

Blood feeding counts on repelled/dead fleas (Week 3)

| Dog no | Group | Day of Study 21 | Paper | No tested | no positive | % positive |
|---|---|---|---|---|---|---|
| | | 21 + 1 h | | | | |
| 449 | B | I | 4 | 4 | 0 | 0% |
| 368 | B | N | 21 | 10 | 5 | 50% |
| 507 | B | F | 20 | 10 | 1 | 10% |
| 483 | B | E | 14 | 10 | 2 | 20% |
| 515 | B | S | 24 | 10 | 1 | 10% |
| 490 | B | T | 19 | 10 | 2 | 20% |
| Mean | | | 17.0 | | | 18% |
| +/−s.d. | | | 7.2 | | | 17% |
| 512 | C | I | 3 | 3 | 0 | 0% |
| 421 | C | N | 14 | 10 | 2 | 20% |
| 234 | C | F | 11 | 10 | 3 | 30% |
| 425 | C | E | 8 | 8 | 2 | 25% |
| 513 | C | S | 9 | 9 | 3 | 33% |
| 312 | C | T | 12 | 10 | 2 | 20% |
| Mean | | | 22 | | | 21% |
| +/−s.d. | | | 3.8 | | | 12% |
| 416 | D | I | 0 | 0 | | |
| 517 | D | N | 0 | 0 | | |
| 470 | D | F | 1 | 1 | 1 | 100% |
| 518 | D | E | 3 | 3 | 2 | 67% |
| 380 | D | S | 1 | 1 | 1 | 100% |
| 504 | D | T | 2 | 2 | 1 | 50% |
| Mean | | | 1.2 | | | 79% |
| +/−s.d. | | | 1.2 | | | 25% |
| 429 | E | I | 28 | 10 | 7 | 70% |
| 412 | E | N | 39 | 10 | 6 | 60% |
| 411 | E | F | 48 | 10 | 10 | 100% |
| 419 | E | E | 30 | 10 | 8 | 80% |
| 378 | E | S | 65 | 10 | 7 | 70% |
| 523 | E | T | 49 | 10 | 10 | 100% |
| Mean | | | 43.2 | | | 80% |
| +/−s.d. | | | 13.8 | | | 17% |
| 517 | F | I | 2 | 2 | 1 | 50% |
| 381 | F | N | 4 | 4 | 3 | 75% |
| 232 | F | F | 1 | 1 | 1 | 100% |
| 427 | F | E | 27 | 10 | 8 | 80% |
| 481 | F | S | 2 | 2 | 1 | 50% |

TABLE 10-continued

Blood feeding counts on repelled/dead fleas (Week 3)

| Dog no | Group | Day of Study 21 | Paper | 21 + 1 h No tested | no positive | % positive |
|---|---|---|---|---|---|---|
| 462 | F | T | 17 | 10 | 7 | 70% |
| Mean | | | 8.8 | | | 71% |
| +/−s.d. | | | 10.7 | | | 19% |

TABLE 11

Blood feeding counts on repelled/dead fleas (Week 4)

| Dog no | Group | Day of Study 28 | Paper | 28 + 1 h No tested | no positive | % positive |
|---|---|---|---|---|---|---|
| 449 | B | I | 6 | 6 | 0 | 0% |
| 368 | B | N | 10 | 10 | 1 | 10% |
| 507 | B | F | 7 | 7 | 0 | 0% |
| 483 | B | E | 8 | 8 | 0 | 0% |
| 515 | B | S | 6 | 6 | 0 | 0% |
| 490 | B | T | 9 | 9 | 0 | 0% |
| Mean | | | 7.7 | | | 2% |
| +/−s.d. | | | 1.6 | | | 4% |
| 512 | C | I | 7 | 7 | 0 | 0% |
| 421 | C | N | 3 | 3 | 0 | 0% |
| 234 | C | F | 5 | 5 | 1 | 20% |
| 425 | C | E | 1 | 1 | 1 | 100% |
| 513 | C | S | 3 | 3 | 0 | 0% |
| 312 | C | T | 6 | 6 | 0 | 0% |
| Mean | | | 22 | | | 20% |
| +/−s.d. | | | 2.2 | | | 40% |
| 416 | D | I | 0 | 0 | | |
| 517 | D | N | 1 | 1 | 1 | 100% |
| 470 | D | F | 2 | 2 | 1 | 50% |
| 518 | D | E | 2 | 2 | 2 | 100% |
| 380 | D | S | 0 | 0 | | |
| 504 | D | T | 5 | 5 | 4 | 80% |
| Mean | | | 1.7 | | | 83% |
| +/−s.d. | | | 1.9 | | | 24% |
| 429 | E | I | 10 | 10 | 7 | 70% |
| 412 | E | N | 32 | 10 | 6 | 60% |
| 411 | E | F | 36 | 10 | 9 | 90% |
| 419 | E | E | 31 | 10 | 10 | 100% |
| 378 | E | S | 51 | 10 | 10 | 100% |
| 523 | E | T | 29 | 10 | 9 | 90% |
| Mean | | | 31.5 | | | 85% |
| +/−s.d. | | | 13.2 | | | 16% |
| 517 | F | I | 0 | 0 | | |
| 381 | F | N | 0 | 0 | | |
| 232 | F | F | 0 | 0 | | |
| 427 | F | E | 5 | 1 | 0 | 0% |
| 481 | F | S | 0 | 0 | | |
| 462 | F | T | 3 | 3 | 3 | 100% |
| Mean | | | 1.3 | | | 50% |
| +/−s.d. | | | 2.2 | | | 71% |

TABLE 12

Blood feeding counts on repelled/dead fleas (Week 5)

| Dog no | Group | Day of Study 35 | Paper | 35 + 1 h No tested | no positive | % positive |
|---|---|---|---|---|---|---|
| 449 | B | I | 10 | 9 | 0 | 0% |
| 368 | B | N | 12 | 10 | 1 | 10% |
| 507 | B | F | 14 | 10 | 0 | 0% |
| 483 | B | E | 11 | 9 | 0 | 0% |
| 515 | B | S | 8 | 10 | 1 | 10% |
| 490 | B | T | 11 | 8 | 0 | 0% |
| Mean | | | 10.9 | | | 3% |
| +/−s.d. | | | 2.0 | | | 5% |
| 512 | C | I | 16 | 10 | 0 | 0% |
| 421 | C | N | 6 | 6 | 0 | 0% |
| 234 | C | F | 12 | 10 | 1 | 10% |
| 425 | C | E | 11 | 10 | 3 | 30% |
| 513 | C | S | 4 | 4 | 1 | 25% |
| 312 | C | T | 10 | 10 | 0 | 0% |
| Mean | | | 4.8 | | | 11% |
| +/−s.d. | | | 4.3 | | | 14% |
| 416 | D | I | 6 | 6 | 5 | 83% |
| 517 | D | N | 4 | 4 | 3 | 75% |
| 470 | D | F | 0 | 0 | | |
| 518 | D | E | 6 | 6 | 5 | 83% |
| 380 | D | S | 2 | 2 | 1 | 50% |
| 504 | D | T | 2 | 2 | 2 | 100% |
| Mean | | | 3.3 | | | 78% |
| +/−s.d. | | | 2.4 | | | 18% |
| 429 | E | I | 7 | 10 | 4 | 40% |
| 412 | E | N | 30 | 10 | 9 | 90% |
| 411 | E | F | 19 | 10 | 7 | 70% |
| 419 | E | E | 23 | 10 | 10 | 100% |
| 378 | E | S | 31 | 10 | 9 | 90% |
| 523 | E | T | 21 | 10 | 8 | 80% |
| Mean | | | 21.8 | | | 78% |
| +/−s.d. | | | 8.7 | | | 21% |
| 517 | F | I | 0 | 0 | | |
| 381 | F | N | 4 | 4 | 4 | 100% |
| 232 | F | F | 1 | 1 | 1 | 100% |
| 427 | F | E | 3 | 0 | | |
| 481 | F | S | 0 | 0 | | |
| 462 | F | T | 8 | 8 | 7 | 88% |
| Mean | | | 2.7 | | 4.0 | 96% |
| +/−s.d. | | | 3.1 | | 3.0 | 7% |

Statistical analyses (Student's "T" test) to determine the significance of apparent differences in flea and tick counts and in blood feeding rates between the groups of treated dogs and the significance of apparent differences in flea and tick counts between these groups and the control group, used the statistical program in Microsoft® Office Professional 2003, version SP3. Probability values less than 0.05 were considered to show statistical significance. Exact probability values were entered down to <0.0001.

Results

The weight ranges, means and standard deviations for the six groups were similar and the mean group weights were in the same locus of the products' weight ranges, occupying a narrow spread of 39% to 43% of the ranges. The fipronil dose rate for groups B, C and D was identical at 10.2 mg/kg, and for group E the dose rate was 11.1 mg/kg. The cyphenothrin dose rates for groups B and C were 8.5 and 5.4 mg/kg, respectively. Some of the products also contained an insect growth regulator (methoprene or pyriproxyfen). At the dose rates applied these IGRs are not known to have any insecticidal/acaricidal efficacy so their presence was not addressed in the calculation of efficacy.

The repellency/speed of kill data for fleas and ticks, are shown in Tables 2-7. The results for blood feeding by fleas on treated dogs are shown in Tables 8-12.

Week 1

The flea counts of all treated groups (Eff#1) showed significant reductions compared with the untreated controls. All treated groups except Group F had significantly smaller tick burdens then the control Group A. At 4 hours, only the cyphenothrin-fortified test substance administered to Group B (9.8% fipronil and 8.2% cyphenothrin) provided adequate efficacy against both fleas and ticks while the substance administered to Group E was adequately effective against only fleas. None of the other test substances attained 90% efficacy against either fleas or ticks at 4 hours although all flea and tick counts on treated dogs were significantly reduced compared with the controls. There were no significant differences in the flea and tick counts between any of the treated groups at 4 hours.

Tray counts of repelled/killed fleas and ticks at 6 hours after treatment were conducted for only Groups B, C and F. While both of the substances used in Groups B and C provided 90% and higher efficacies against fleas and ticks, the substance administered to Group F failed to attain the threshold value for either parasite. The cyphenothrin-fortified test substance (Group B) had significantly fewer fleas than that used on Group C or Group F and significantly fewer ticks than Group C. All test substances attained 90% or better efficacy at 24 and 48 hours after treatment (Eff#1 values).

Conclusions for Week 1:

Consistently significant quick kill/repellency against fleas and ticks was shown by only the cyphenothrin-fortified test substance and the substance used in Group E. The efficacy of the substance used in Group F against both fleas and ticks at 6 hours was lower than the cyphenothrin-fortified test substance (Group B), which was significantly more effective against both fleas and ticks than that used in Group C and significantly more effective against fleas than that used in Group F.

Week 2

At 1 hour after re-infestation with new fleas and ticks (*D. variabilis*) on day 8, the substance used in Group E performed the best. At 4 hours all products were effective against fleas but only the Group E and Group F substances were adequately effective against the new ticks. At 6 hours, the flea counts for Groups B, C and F were reduced by at least 90%, and the fortified test substance (Group B) and the substance used in Group F were adequately effective against ticks. At 24 and 48 hours after re-infestation all test substances were 100% effective against fleas and ticks. Flea and tick burdens on all treated dogs on days 8, 9 and 10 were significantly reduced compared with the untreated controls, except for the tick counts on the dogs in Group D that were not significantly different (P>0.1) from the tick counts on the untreated controls at 1 hour.

Conclusions for Week 2:

The data shows quick killing/repellency for fleas for all test substances, based on the 4 hour results. The data for the substances administered in Groups B, E, and F (but not in Groups C or D) show quick killing/repellency also for ticks. The 6 hour data shows 90% or better efficacy against fleas and ticks for the substances administered in Group B and Group F, but only for fleas on dogs treated in Group C.

Week 3

Although all flea and tick counts on treated dogs were invariably significantly smaller than the counts on the untreated controls, at 4 hours after re-infestation with new fleas and ticks (*R. sanguineus*) on day 14, the efficacies of the fortified test substance used in Group B and the substance used in Group F met the threshold for quick kill/repels against both parasites. Comparing treated groups at 1 hour, Group E had significantly smaller flea burdens than all other treated groups. Tick counts at 1 and 4 hours on the dogs treated with the fortified test substance (Group B) were highly significantly smaller than the count on dogs treated in Group C, which exhibits the improvement potential of increasing the cyphenothrin component from 5.2% to 8.2%. The cyphenothrin-fortified test substance (Group B) was also significantly more effective in reducing tick burdens at 1 and 4 hours compared with Group D and also compared with Group E at 1 hour. The substance used in Group E was more effective against ticks at 1 and 4 hours compared with Group D and at 1 hour against ticks, compared with Group F. While efficacy values for all test substances at 24 and 48 hours was significant, there were significant differences at 24 hours in tick burdens since dogs treated with the test substances (Groups B and C) and with the substance Group E carried significantly fewer ticks the Group D and Group E dogs.

Conclusions for Week 3:

The data shows consistently better quick killing/repellency against both fleas and ticks for only the cyphenothrin-fortified test substance (Group B) and for the substance used in Group E.

Week 4

At both 1 and 4 hours after re-infestation with new fleas and ticks on day 21, none of the flea and tick burdens on any of the treated dogs were reduced significantly. At 1 hour the flea counts on only Groups E and F dogs and the tick counts on only Groups B, C, and E dogs were significantly smaller than on the controls. At 4 hours all flea and tick counts on treated dogs were significantly smaller than on the controls. The tick counts at 4 hours on Groups B, C, and E were significantly smaller than the tick counts on the dogs of Groups D and F. At 6 hours after re-infestation on day 21, although there were no significant differences in the flea and tick burdens between any of the three groups of treated dogs, the two fipronil/cyphenothrin substances (Groups B and C) were adequately efficacious against flea and ticks while the Group F substance failed to attain 90% efficacy against either fleas or ticks. At 24 and 48 hours, on days 22 and 23 all test substances were 100% effective against fleas and ticks.

Conclusions for Week 4:

At 4 hours, the two fipronil/cyphenothrin substances (Groups B and C) and the substance used in Group E were all significantly more effective in quickly killing and repelling ticks, compared with both of the substances used in Groups D and F. At 6 hours dogs treated with the fipronil/cyphenothrin substances (Groups B and C) had fewer fleas and ticks than the Group F treated dogs.

Week 5

At 1 hour the flea counts on the subjects treated with the substance in Group E were significantly smaller than the counts on all other treated groups while tick counts on the dogs treated with the cyphenothrin-fortified test substance (Group B) or with the substance in Group E were significantly smaller than the counts on the dogs treated with either of the substances used in Group D or Group F. At 24 and 48 hours, the flea and tick counts on all groups of treated dogs were significantly smaller than on the untreated controls. Statistically, the substances used in Groups B, C and F were more efficacious against fleas at 24 hours than that used in Group E and at 48 hours, the substances used in Group C and Group D were more efficacious than Group E. There were no significant differences between the treated groups' tick burdens at 24 and 48 hours.

Conclusions for Week 5:

The efficacies of all test substances against fleas and ticks support effectiveness for 1 month.

Week 6

Following re-infestation with new fleas and ticks on day 35, the numbers of ticks on the dogs treated with the two fipronil/cyphenothrin substances (Groups B and C) were significantly lower at 1, 4 and 24 hours compared with the Group D substance. At 1 and 4 hours the flea counts on the dogs treated with the Group C substance were significantly lower than on the dogs treated with the Group D substance. The tick counts on the dogs treated with the Group E substance were smaller than on the dogs treated with the Group C substance, the Group D substance, and the Group F substance.

Conclusions for Week 6:

The results support residual efficacy of 5 weeks against both fleas and ticks for all test substances.

As can be seen from the empirical data presented above, only treatment with the two fipronil/cyphenothrin substances (Groups B and C) resulted in greater average kill rates and speed of kill for ticks at 1 hour, 4 hours, 6 hours following treatment when compared to the other products, and superior kill rates with the combination of fipronil and cyphenothrin persisted after subsequent reinfestations of the host dogs with both fleas and ticks, up to 6 weeks after the initial application of the spot-on compositions.

Flea Blood Feeding Test

Group mean percent of fleas containing evidence of blood feeding varied from a low of 2% (Group B) to a high of 90% (Group F). Statistical analysis of aggregated group blood-fed values between the five groups of treated dogs (Student's "T" test, two tailed, assuming unequal variances), showed that the two fipronil/cyphenothrin substances (Groups B and C) had very highly significantly reduced blood feeding by fleas ($P<0.0001$), compared with the other three groups of treated dogs (Groups D, E and F) and there were no significant differences in blood feeding rates between these three groups ($P>0.1$). Analyses of the blood feeding data, comparing the aggregate Group C results (mean 37%+/−S.D. 27%) with this product when fortified with additional cyphenothrin as in Group B (11%+/−13%) showed that the fortified product was much more efficacious in preventing flea feeding at a very highly significant degree ($P<0.0001$).

As can be seen from the empirical data presented above, treatment with the combined fipronil and cyphenothrin formulations resulted in increased efficacy against blood feeding than the other formulations.

Example 2

Immediate and Residual Efficacies Following Application of a Squeeze-on Containing Cyphenothrin and Pyriproxyfen and a Squeeze-on for Dogs Containing Fipronil and Cyphenothrin Compared with a Squeeze-on Containing Etofenprox, Methoprene and Piperonyl Butoxide, Against Fleas (*Ctenocephalides felis*) and Ticks (*Rhipicephalus sanguineus* and *Dermacentor variabilis*) on Dogs A cyphenothrin-based test substance containing 20% cyphenothrin and 2% pyriproxyfen was compared for efficacy to (1) a squeeze-on composition containing 5.2% cyphenothrin and 9.8% fipronil, and (2) a squeeze-on composition containing 30% etofenprox, 5% piperonyl butoxide and 3.6% (s)-methoprene. Each composition was applied once, was evaluated and compared for efficacy against infestations of fleas and ticks (*Rhipicephalus sanguineus* and *Dermacentor variabilis*). Immediate efficacy against existing fleas and ticks and residual efficacies against flea and tick re-infestations, applied weekly, were measured over 37 days following treatment. Flea and tick counts on the dogs were performed at 5 and 15 minutes, at 1 and 4 hours and at 24 and 48 hours after treatment and similarly after each re-infestation. Killed and repelled parasites were recovered at 5 and 15 minutes and at 1 and 4 hours after treatment and after each re-infestation to measure speed of kill and repellency.

All three squeeze-on products started killing existing and new fleas within 5 to 15 minutes. The data also supported killing and repelling existing and new fleas within 1 to 4 hours. The results with ticks, however, were different showing superior performance for the cyphenothrin-based substances as compared with the etofenprox-based substance. The etofenprox-based substance took 4 times longer (about 1 hour) to start killing existing and new ticks (in absence of relevant guidelines at an arbitrary 50% efficacy threshold) than did the cyphenothrin-based products. The data for the etofenprox-based substance did not support any claims of quick kill/repellency (at the 90% EPA threshold) for existing or for new ticks. The etofenprox-based substance also failed to produce adequate reductions in new tick counts to support a general efficacy claim against ticks when the treated dogs were re-infested on day 21.

The blood feeding data from killed and repelled fleas collected up to 4 hours after re-infestation showed that the substance containing high concentration (20%) of cyphenothrin prevented fleas from laying eggs before they were killed and repelled. Egg production occurred from dogs treated with the substance containing low concentration of cyphenothrin (5.2%) but at a level that was at least half that observed from dogs treated with the etofenprox-based substance. All three products completely prevented new fleas from laying eggs before they were killed for 1 month after treatment.

Treatment Grouping and Infestation Schedule

The grouping of the test subjects and their treatment dosages are as follows. Dogs weighing between approximately 20 lb and 36 lb were allocated to 4 groups, as set forth in Table 13.

TABLE 13

Grouping and Treatment

| Group | Weight | Treatment |
| --- | --- | --- |
| A | 20 lb-36 lb | None |
| B | 20 lb-36 lb | 20% cyphenothrin/2% pyriproxyfen |
| C | 20 lb-36 lb | 5.2% cyphenothrin/9.8% fipronil |
| D | 20 lb-36 lb | 30% etofenprox/5% piperonyl butoxide/3.6% (s)-methoprene |

Six dogs in Group A were untreated controls. The high concentration cyphenothrin substance was applied to the 6 dogs of Group B, the fipronil/low concentration cyphenothrin substance was applied to the 6 dogs in Group B and etofenprox-based substance was applied to the six dogs in Group D. All three products were applied from their commercial packages, in accordance with the respective label directions.

The dogs were infested with 100 fleas and 50 ticks on days −1, 7, 14, 21, 27 and 35. Flea specie was the cat flea *Ctenocephalides felis* and tick species were *Rhipicephalus sanguineus* and *Dermacentor variabilis*, alternated at each successive re-infestation.

Flea and tick counts were conducted at 5 and 15 minutes, then at 1 and 4 hours and finally at 24 and 48 hours after treatment and after re-infestation. The fleas and ticks were not removed or damaged by "hand" counting at all counts, except for the comb counts conducted at 48 hours when all parasites were removed and destroyed. Before treatment and before each re-infestation, the soil trays beneath the dogs were fitted with white paper liners to enable recovery and counting of killed and repelled fleas and ticks and recovery of flea eggs that fell off the dogs during each pre-count interval. The repelled and killed fleas, so collected, were squashed on moist white paper to detect the presence of the hosts' blood indicating whether the fleas had taken a blood meal.

Efficacy against fleas and ticks was calculated at each time point using the following formulae.

1. Immediate efficacy/speed of kill for each treated dog was the reduction in live parasite burden at 5 and 15 minutes and at 1 and 4 hours, compared with and expressed as percent of the mean control group burden, without reference to the numbers of killed and repelled fleas and ticks accumulated on the paper liners (summarized in Tables 14-19 as "Eff #1"), as follows:

$$\frac{\text{Mean number of live fleas/ticks on untreated dogs} - \text{Number of live fleas/ticks on each treated dog} \times 100}{\text{Mean number of live fleas/ticks on untreated dogs}}$$

2. The second method was to calculate the numbers of parasites found dead on each dog combined with the numbers of killed/repelled parasites on the paper liners as a percent of the total parasite burden for that dog, at 5 and 15 minutes and at 1 and 4 hours, accumulated at each time point, as follows:

$$\frac{\text{Number of killed/repelled fleas/ticks from each treated dog} \times 100}{\text{Number of live fleas/ticks on that dog} + \text{number of killed/repelled fleas/ticks}}.$$

3. The second formula based on tray counts does not, however, take into consideration the numbers of parasites that, for unknown reasons unrelated to any treatment, will progressively fall off the dog and/or die and therefore negates the value of having untreated control dogs. In order to adjust for this "normal" parasite attrition, tray counts for repelled/killed parasites are also conducted for each untreated control with individual "efficacy" values derived as above. The mean group efficacy value for treatment is then adjusted/reduced by the contemporaneous "normal attrition efficacy" to provide controlled group efficacy values attributable to only treatment (summarized in Tables 14-19 as "Eff#2"), as follows:

Group means percent value of $$\frac{[\text{Number of killed/repelled fleas/ticks on liner below each treated dog} \times 100]}{\text{Number of fleas/ticks on that dog} + \text{number of killed/repelled fleas/ticks}\}$$

Minus group mean percent value of $$\frac{[\text{Number of killed/repelled fleas/ticks on liner below each control dog} \times 100]}{\text{Number of live fleas/ticks on that dog} + \text{number of killed/repelled fleas/ticks}\}$$

4. Efficacy at 24 and 48 hours was calculated as follows:

$$\frac{\text{Mean number of live fleas/ticks on untreated dogs} - \text{Number of live fleas/ticks on each treated dog} \times 100}{\text{Mean number of live fleas/ticks on untreated dogs}}.$$

5. Efficacy in preventing flea feeding was measured at the 5 and 15 minutes and 1 and 4 hours counts, as percentage of each dog's killed and repelled fleas containing blood, with mean group feeding percentage then calculated (Tables 20-24).

6. Estimates were made of the numbers of flea eggs that had been deposited on the paper liners at 5 and 15 minutes and at 1 and 4 hours after each re-infestation (Tables 25-29).

TABLE 14

Summary Mean Group Efficacies against Fleas and Ticks (Day 0)

| Group | Test | | -1 | 0 | @ 5 min*<br>% effic | @ 15 min*<br>% effic | @ 1 hour*<br>% effic | @ 4 hours*<br>% effic | 1 *<br>% effic | 2<br>% effic |
|---|---|---|---|---|---|---|---|---|---|---|
| B | Fleas | Eff #1 | I | T | 62% | 71% | 98% | 100% | 100% | 100% |
|   |       | Eff #2 | N | R | 18% | 52% | 98% | 99% |   |   |
|   | Ticks | Eff #1 | F | E | −43% | 66% | 87% | 97% | 100% | 100% |
|   |       | Eff #2 | E | A | 14% | 61% | 87% | 95% |   |   |
| C | Fleas | Eff #1 | S | T | 52% | 72% | 84% | 99% | 100% | 100% |
|   |       | Eff #2 | T |   | 15% | 63% | 80% | 99% |   |   |
|   | Ticks | Eff #1 |   |   | −9% | 67% | 80% | 96% | 99% | 100% |
|   |       | Eff #2 |   |   | 11% | 44% | 72% | 95% |   |   |
| D | Fleas | Eff #1 |   |   | 61% | 72% | 92% | 100% | 100% | 100% |
|   |       | Eff #2 |   |   | 9% | 57% | 87% | 100% |   |   |
|   | Ticks | Eff #1 |   |   | −3% | 36% | 54% | 83% | 98% | 100% |
|   |       | Eff #2 |   |   | 7% | 7% | 36% | 84% |   |   |

Bold entries meet EPA 90% minimum efficacy for claims.

1 Efficacy formula is (mean parasites on controls − parasites on treated dog)/(mean control parasite count) %, independent of tray counts of repelled/killed parasites.

2 Efficacy formula includes ad

TABLE 15

Summary Mean Group Efficacies against Fleas and Ticks (Day 7)

| Days Group | Test | | 7 | @ 5 min* % effic | @ 15 min* % effic | @ 1 hour* % effic | @ 4 hours* % effic | 8 * % effic | 9 % effic | Days Group |
|---|---|---|---|---|---|---|---|---|---|---|
| B | Fleas | Eff #1 | I | 82% | 100% | 100% | 100% | 100% | 100% | B |
|   |       | Eff #2 | N | 49% | 100% | 100% | 100% |   |   |   |
|   | Ticks | Eff #1 | F | 79% | 100% | 100% | 100% | 100% | 100% |   |
|   |       | Eff #2 | E | 80% | 98% | 98% | 98% |   |   |   |
| C | Fleas | Eff #1 | S | 62% | 92% | 100% | 100% | 100% | 100% | C |
|   |       | Eff #2 | T | 38% | 87% | 100% | 100% |   |   |   |
|   | Ticks | Eff #1 |   | 58% | 93% | 100% | 100% | 100% | 100% |   |
|   |       | Eff #2 |   | 60% | 92% | 98% | 98% |   |   |   |
| D | Fleas | Eff #1 |   | 59% | 80% | 93% | 100% | 100% | 100% | D |
|   |       | Eff #2 |   | 4% | 40% | 83% | 100% |   |   |   |
|   | Ticks | Eff #1 |   | 30% | 41% | 69% | 89% | 100% | 100% |   |
|   |       | Eff #2 |   | 16% | 35% | 67% | 86% |   |   |   |

Bold entries meet EPA 90% minimum efficacy for claims.
1 Efficacy formula is (mean parasites on controls − parasites on treated dog)/(mean control parasite count) %, independent of tray counts of repelled/killed parasites.
2 Efficacy formula includes ad

TABLE 16

Summary Mean Group Efficacies against Fleas and Ticks (Day 14)

| Days Group | Test | | 14 | @ 5 min* % effic | @ 15 min* % effic | @ 1 hour* % effic | @ 4 hours* % effic | 15 * % effic | 16 % effic |
|---|---|---|---|---|---|---|---|---|---|
| B | Fleas | Eff #1 | I | 64% | 94% | 100% | 100% | 100% | 100% |
|   |       | Eff #2 | N | 72% | 95% | 99% | 99% |   |   |
|   | Ticks | Eff #1 | F | 74% | 97% | 100% | 100% | 100% | 100% |
|   |       | Eff #2 | E | 64% | 81% | 86% | 85% |   |   |
| C | Fleas | Eff #1 | S | 46% | 76% | 82% | 99% | 100% | 100% |
|   |       | Eff #2 | T | 64% | 85% | 90% | 98% |   |   |
|   | Ticks | Eff #1 |   | 86% | 96% | 97% | 100% | 100% | 100% |
|   |       | Eff #2 |   | 81% | 85% | 83% | 85% |   |   |
| D | Fleas | Eff #1 |   | 39% | 91% | 95% | 97% | 100% | 100% |
|   |       | Eff #2 |   | 58% | 92% | 95% | 97% |   |   |
|   | Ticks | Eff #1 |   | 63% | 75% | 85% | 91% | 95% | 99% |
|   |       | Eff #2 |   | 57% | 63% | 72% | 78% |   |   |

Bold entries meet EPA 90% minimum efficacy for claims.
1 Efficacy formula is (mean parasites on controls − parasites on treated dog)/(mean control parasite count) %, independent of tray counts of repelled/killed parasites.
2 Efficacy formula includes ad

TABLE 17

Summary Mean Group Efficacies against Fleas and Ticks (Day 21)

| Days Group | Test | | 21 | @ 5 min* % effic | @ 15 min* % effic | @ 1 hour* % effic | @ 4 hours* % effic | 22 * % effic | 23 % effic | Days Group |
|---|---|---|---|---|---|---|---|---|---|---|
| B | Fleas | Eff #1 | I | 58% | 85% | 98% | 100% | 100% | 100% | B |
|   |       | Eff #2 | N | 65% | 85% | 98% | 100% |   |   |   |
|   | Ticks | Eff #1 | F | 38% | 91% | 100% | 100% | 100% | 100% |   |
|   |       | Eff #2 | E | 37% | 87% | 95% | 95% |   |   |   |
| C | Fleas | Eff #1 | S | 28% | 61% | 82% | 100% | 100% | 100% | C |
|   |       | Eff #2 | T | 47% | 63% | 84% | 100% |   |   |   |
|   | Ticks | Eff #1 |   | 31% | 58% | 84% | 97% | 100% | 100% |   |
|   |       | Eff #2 |   | 21% | 52% | 79% | 92% |   |   |   |
| D | Fleas | Eff #1 |   | 37% | 64% | 88% | 99% | 100% | 100% | D |
|   |       | Eff #2 |   | 39% | 54% | 84% | 99% |   |   |   |
|   | Ticks | Eff #1 |   | 25% | 37% | 58% | 78% | 80% | 84% |   |
|   |       | Eff #2 |   | 15% | 26% | 48% | 44% |   |   |   |

Bold entries meet EPA 90% minimum efficacy for claims.
1 Efficacy formula is (mean parasites on controls − parasites on treated dog)/(mean control parasite count) %, independent of tray counts of repelled/killed parasites.
2 Efficacy formula includes ad

TABLE 18

Summary Mean Group Efficacies against Fleas and Ticks (Day 28)

| Group | Test | | 28 Days | @ 5 min* % effic | @ 15 min* % effic | @ 1 hour* % effic | @ 4 hours* % effic | 28 * % effic | 29 % effic |
|---|---|---|---|---|---|---|---|---|---|
| B | Fleas | Eff #1 | I | 56% | 91% | 100% | 100% | 100% | 100% |
|   |   | Eff #2 | N | 65% | 93% | 100% | 100% |   |   |
|   | Ticks | Eff #1 | F | 72% | 95% | 100% | 100% | 100% | 100% |
|   |   | Eff #2 | E | 71% | 93% | 96% | 96% |   |   |
| C | Fleas | Eff #1 | S | 62% | 77% | 95% | 99% | 100% | 100% |
|   |   | Eff #2 | T | 46% | 69% | 93% | 99% |   |   |
|   | Ticks | Eff #1 |   | 60% | 80% | 93% | 95% | 100% | 100% |
|   |   | Eff #2 |   | 56% | 77% | 89% | 91% |   |   |
| D | Fleas | Eff #1 |   | 58% | 76% | 92% | 100% | 99% | 100% |
|   |   | Eff #2 |   | 47% | 69% | 90% | 100% |   |   |
|   | Ticks | Eff #1 |   | 51% | 65% | 76% | 79% | 80% | 91% |
|   |   | Eff #2 |   | 44% | 56% | 67% | 70% |   |   |

Bold entries meet EPA 90% minimum efficacy for claims.
1 Efficacy formula is (mean parasites on controls − parasites on treated dog)/(mean control parasite count) %, independent of tray counts of repelled/killed parasites.
2 Efficacy formula includes ad

TABLE 19

Summary Mean Group Efficacies against Fleas and Ticks (Day 35)

| Group | Test | | 35 Days | @ 5 min* % effic | @ 15 min* % effic | @ 1 hour* % effic | @ 4 hours* % effic | 36 * % effic | 37 % effic |
|---|---|---|---|---|---|---|---|---|---|
| B | Fleas | Eff #1 | I | 44% | 70% | 91% | 100% | 100% | 100% |
|   |   | Eff #2 | N | 38% | 45% | 86% | 100% |   |   |
|   | Ticks | Eff #1 | F | 32% | 71% | 95% | 97% | 100% | 100% |
|   |   | Eff #2 | E | 30% | 66% | 93% | 95% |   |   |
| C | Fleas | Eff #1 | S | 36% | 58% | 81% | 99% | 100% | 100% |
|   |   | Eff #2 | T | 17% | 34% | 68% | 98% |   |   |
|   | Ticks | Eff #1 |   | 30% | 39% | 78% | 97% | 100% | 100% |
|   |   | Eff #2 |   | 17% | 29% | 72% | 95% |   |   |
| D | Fleas | Eff #1 |   | 44% | 69% | 95% | 97% | 100% | 100% |
|   |   | Eff #2 |   | 31% | 46% | 92% | 94% |   |   |
|   | Ticks | Eff #1 |   | 32% | 42% | 52% | 72% | 97% | 99% |
|   |   | Eff #2 |   | 11% | 16% | 28% | 54% |   |   |

Bold entries meet EPA 90% minimum efficacy for claims.
1 Efficacy formula is (mean parasites on controls − parasites on treated dog)/(mean control parasite count) %, independent of tray counts of repelled/killed parasites.
2 Efficacy formula includes ad

TABLE 20

Immediate and residual efficacies. Blood feeding summary (Day 7)

| Dog no | Group | | Day of Study 7 | 5 min % positive | 15 min % positive | 1 hour % positive | 4 hours % positive |
|---|---|---|---|---|---|---|---|
| Mean | B | T | I | 0% | 0% | * | * |
| Mean | C | R | N | 0% | 5% | 49% | 100% |
| Mean | D | T | F | 0% | 51% | 80% | 84% |

* no fleas were shed or there were no fleas left on the dogs so there were no killed and repelled fleas to be examined

TABLE 21

Immediate and residual efficacies. Blood feeding summary (Day 14)

| Dog no | Group | Day of Study 14 | 5 min % positive | 15 min % positive | 1 hour % positive | 4 hours % positive |
|---|---|---|---|---|---|---|
| Mean | B | I | 0% | 0% | 0% | * |
| Mean | C | N | 0% | 0% | 35% | 25% |
| Mean | D | F | 0% | 34% | 61% | * |

* no fleas were shed or there were no fleas left on the dogs so there were no killed and repelled fleas to be examined

TABLE 22

Immediate and residual efficacies. Blood feeding summary (Day 21)

| Dog no | Group | Day of Study 21 | 5 min % positive | 15 min % positive | 1 hour % positive | 4 hours % positive |
|---|---|---|---|---|---|---|
| Mean | B | I | * | 0% | 0% | 0% |
| Mean | C | N | 0% | 0% | 5% | 28% |
| Mean | D | F | 37% | 43% | 58% | 70% |

* no fleas were shed or there were no fleas left on the dogs so there were no killed and repelled fleas to be examined

TABLE 23

Immediate and residual efficacies. Blood feeding summary (Day 28)

| Dog no | Group | Day of Study 28 | 5 min % positive | 15 min % positive | 1 hour % positive | 4 hours % positive |
|---|---|---|---|---|---|---|
| Mean | B | I | 0% | 0% | 0% | * |
| Mean | C | N | 0% | 7% | 49% | 58% |
| Mean | D | F | 0% | 50% | 76% | 95% |

* no fleas were shed or there were no fleas left on the dogs so there were no killed and repelled fleas to be examined

TABLE 24

Immediate and residual efficacies.
Blood feeding summary (Day 35)

| Dog no | Group | Day of Study 35 | 5 min % positive | 15 min % positive | 1 hour % positive | 4 hours % positive |
|---|---|---|---|---|---|---|
| Mean | B | I | 0% | 12% | 20% | 88% |
| Mean | C | N | 0% | 22% | 57% | 70% |
| Mean | D | F | 3% | 55% | 82% | 86% |

* no fleas were shed or there were no fleas left on the dogs so there were no killed and repelled fleas to be examined

TABLE 25

Estimated flea egg laying (Day 7)

| Dog no | Group | Day of Study 7 | 5 min | 15 min | 1 hour | 4 hours |
|---|---|---|---|---|---|---|
| 510 | A | I | 5 | 0 | 0 | 30 |
| 357 | A | N | 8 | 0 | 30 | 100 |
| 509 | A | F | 10 | 0 | 0 | 60 |
| 236 | A | E | 10 | 0 | 50 | 75 |
| 393 | A | S | 15 | 0 | 40 | 60 |
| 448 | A | T | 10 | 0 | 50 | 100 |
| Mean | | | 9.7 | 0.0 | 28.3 | 71 |
| +/−s.d. | | | 3.3 | 0.0 | 23.2 | 27 |
| 470 | B | I | 0 | 0 | 0 | 0 |
| 381 | B | N | 0 | 0 | 0 | 0 |
| 232 | B | F | 0 | 0 | 0 | 0 |
| 462 | B | E | 0 | 0 | 0 | 0 |
| 425 | B | S | 0 | 0 | 0 | 0 |
| 513 | B | T | 0 | 0 | 0 | 0 |
| Mean | | | 0.0 | 0.0 | 0.0 | 0% |
| +/−s.d. | | | 0.0 | 0.0 | 0.0 | 0% |
| 481 | C | I | 0 | 0 | 0 | 0 |
| 419 | C | N | 0 | 0 | 0 | 0 |
| 378 | C | F | 0 | 0 | 0 | 0 |
| 380 | C | E | 0 | 0 | 0 | 0 |
| 504 | C | S | 0 | 0 | 0 | 0 |
| 523 | C | T | 0 | 0 | 0 | 0 |
| Mean | | | 0.0 | 0.0 | 0.0 | 0% |
| +/−s.d. | | | 0.0 | 0.0 | 0.0 | 0% |
| 381 | D | I | 0 | 0 | 0 | 0 |
| 234 | D | N | 0 | 0 | 0 | 0 |
| 412 | D | F | 0 | 0 | 0 | 0 |
| 515 | D | E | 0 | 0 | 0 | 0 |
| 411 | D | S | 0 | 0 | 0 | 0 |
| 312 | D | T | 0 | 0 | 0 | 0 |
| Mean | | | 0.0 | 0.0 | 0.0 | 0% |
| +/−s.d. | | | 0.0 | 0.0 | 0.0 | 0% |

TABLE 26

Estimated flea egg laying (Day 14)

| Dog no | Group | Day of Study 14 | 5 min | 15 min | 1 hour | 4 hours |
|---|---|---|---|---|---|---|
| 510 | A | I | 10 | 5 | 25 | 75 |
| 357 | A | N | 5 | 0 | 40 | 100 |
| 509 | A | F | 0 | 5 | 35 | 80 |
| 236 | A | E | 10 | 10 | 50 | 70 |
| 393 | A | S | 5 | 10 | 45 | 70 |
| 448 | A | T | 10 | 10 | 35 | 45 |
| Mean | | | 7 | 7 | 38 | 73 |
| +/−s.d. | | | 4 | 4 | 9 | 18 |
| 470 | B | I | 0 | 0 | 0 | 0 |
| 381 | B | N | 0 | 0 | 0 | 0 |
| 232 | B | F | 0 | 0 | 0 | 0 |
| 462 | B | E | 0 | 0 | 0 | 0 |
| 425 | B | S | 0 | 0 | 0 | 0 |
| 513 | B | T | 0 | 0 | 0 | 0 |
| Mean | | | 0.0 | 0.0 | 0.0 | 0% |
| +/−s.d. | | | 0.0 | 0.0 | 0.0 | 0% |
| 481 | C | I | 0 | 0 | 0 | 0 |
| 419 | C | N | 0 | 0 | 0 | 0 |
| 378 | C | F | 0 | 0 | 0 | 0 |
| 380 | C | E | 0 | 0 | 0 | 0 |
| 504 | C | S | 0 | 0 | 0 | 0 |
| 523 | C | T | 0 | 0 | 0 | 0 |
| Mean | | | 0.0 | 0.0 | 0.0 | 0% |
| +/−s.d. | | | 0.0 | 0.0 | 0.0 | 0% |
| 381 | D | I | 0 | 0 | 0 | 0 |
| 234 | D | N | 0 | 0 | 0 | 0 |
| 412 | D | F | 0 | 0 | 0 | 0 |
| 515 | D | E | 0 | 0 | 0 | 0 |
| 411 | D | S | 0 | 0 | 0 | 0 |
| 312 | D | T | 0 | 0 | 0 | 0 |
| Mean | | | 0.0 | 0.0 | 0.0 | 0% |
| +/−s.d. | | | 0.0 | 0.0 | 0.0 | 0% |

TABLE 27

Estimated flea egg laying (Day 21)

| Dog no | Group | Day of Study 21 | 5 min | 15 min | 1 hour | 4 hours |
|---|---|---|---|---|---|---|
| 510 | A | I | 5 | 5 | 35 | 55 |
| 357 | A | N | 10 | 5 | 45 | 60 |
| 509 | A | F | 0 | 10 | 45 | 50 |
| 236 | A | E | 10 | 5 | 30 | 40 |
| 393 | A | S | 15 | 10 | 40 | 50 |
| 448 | A | T | 10 | 5 | 40 | 50 |
| Mean | | | 8 | 7 | 39 | 51 |
| +/−s.d. | | | 5 | 3 | 6 | 7 |
| 470 | B | I | 0 | 0 | 0 | 0 |
| 381 | B | N | 0 | 0 | 0 | 0 |
| 232 | B | F | 0 | 0 | 0 | 0 |
| 462 | B | E | 0 | 0 | 0 | 0 |
| 425 | B | S | 0 | 0 | 0 | 0 |
| 513 | B | T | 0 | 0 | 0 | 0 |
| Mean | | | 0.0 | 0.0 | 0.0 | 0% |
| +/−s.d. | | | 0.0 | 0.0 | 0.0 | 0% |
| 481 | C | I | 0 | 0 | 0 | 0 |
| 419 | C | N | 0 | 0 | 0 | 0 |
| 378 | C | F | 0 | 0 | 0 | 0 |
| 380 | C | E | 0 | 0 | 0 | 0 |
| 504 | C | S | 0 | 0 | 0 | 0 |
| 523 | C | T | 0 | 0 | 0 | 0 |
| Mean | | | 0.0 | 0.0 | 0.0 | 0% |
| +/−s.d. | | | 0.0 | 0.0 | 0.0 | 0% |
| 381 | D | I | 0 | 0 | 0 | 0 |
| 234 | D | N | 0 | 0 | 0 | 0 |
| 412 | D | F | 0 | 0 | 0 | 0 |
| 515 | D | E | 0 | 0 | 0 | 0 |
| 411 | D | S | 0 | 0 | 0 | 0 |
| 312 | D | T | 0 | 0 | 0 | 0 |
| Mean | | | 0.0 | 0.0 | 0.0 | 0% |
| +/−s.d. | | | 0.0 | 0.0 | 0.0 | 0% |

TABLE 28

Estimated flea egg laying (Day 28)

| Dog no | Group | Day of Study 28 | No flea eggs @ time after re-infestation | | | |
|---|---|---|---|---|---|---|
| | | | 5 min | 15 min | 1 hour | 4 hours |
| 510 | A | I | 10 | 5 | 30 | 40 |
| 357 | A | N | 15 | 5 | 25 | 30 |
| 509 | A | F | 5 | 10 | 25 | 35 |
| 236 | A | E | 41 | 10 | 35 | 40 |
| 393 | A | S | 5 | 15 | 40 | 40 |
| 448 | A | T | 5 | 10 | 25 | 35 |
| Mean | | | 14 | 9 | 30 | 37 |
| +/−s.d. | | | 14 | 4 | 6 | 4 |
| 470 | B | I | 0 | 0 | 0 | 0 |
| 381 | B | N | 0 | 0 | 0 | 0 |
| 232 | B | F | 0 | 0 | 0 | 0 |
| 462 | B | E | 0 | 0 | 0 | 0 |
| 425 | B | S | 0 | 0 | 0 | 0 |
| 513 | B | T | 0 | 0 | 0 | 0 |
| Mean | | | 0.0 | 0.0 | 0.0 | 0% |
| +/−s.d. | | | 0.0 | 0.0 | 0.0 | 0% |
| 481 | C | I | 0 | 0 | 0 | 0 |
| 419 | C | N | 0 | 0 | 0 | 0 |
| 378 | C | F | 0 | 0 | 0 | 0 |
| 380 | C | E | 0 | 0 | 0 | 0 |
| 504 | C | S | 0 | 0 | 0 | 0 |
| 523 | C | T | 0 | 0 | 0 | 0 |
| Mean | | | 0.0 | 0.0 | 0.0 | 0% |
| +/−s.d. | | | 0.0 | 0.0 | 0.0 | 0% |
| 381 | D | I | 0 | 0 | 0 | 0 |
| 234 | D | N | 0 | 0 | 0 | 0 |
| 412 | D | F | 0 | 0 | 0 | 0 |
| 515 | D | E | 0 | 0 | 0 | 0 |
| 411 | D | S | 0 | 0 | 0 | 0 |
| 312 | D | T | 0 | 0 | 0 | 0 |
| Mean | | | 0.0 | 0.0 | 0.0 | 0% |
| +/−s.d. | | | 0.0 | 0.0 | 0.0 | 0% |

TABLE 29

Estimated flea egg laying (Day 35)

| Dog no | Group | Day of Study 35 | No flea eggs @ time after re-infestation | | | |
|---|---|---|---|---|---|---|
| | | | 5 min | 15 min | 1 hour | 4 hours |
| 510 | A | I | 15 | 5 | 25 | 40 |
| 357 | A | N | 5 | 10 | 30 | 40 |
| 509 | A | F | 5 | 15 | 30 | 40 |
| 236 | A | E | 5 | 15 | 35 | 45 |
| 393 | A | S | 10 | 10 | 40 | 45 |
| 448 | A | T | 5 | 10 | 30 | 35 |
| Mean | | | 8 | 11 | 32 | 41 |
| +/−s.d. | | | 4 | 4 | 5 | 4 |
| 470 | B | I | 0 | 0 | 0 | 0 |
| 381 | B | N | 0 | 0 | 0 | 0 |
| 232 | B | F | 0 | 0 | 0 | 0 |
| 462 | B | E | 0 | 0 | 0 | 0 |
| 425 | B | S | 0 | 0 | 0 | 0 |
| 513 | B | T | 0 | 0 | 0 | 0 |
| Mean | | | 0.0 | 0.0 | 0.0 | 0% |
| +/−s.d. | | | 0.0 | 0.0 | 0.0 | 0% |
| 481 | C | I | 0 | 0 | 0 | 0 |
| 419 | C | N | 0 | 0 | 0 | 0 |
| 378 | C | F | 0 | 0 | 0 | 0 |
| 380 | C | E | 0 | 0 | 0 | 0 |
| 504 | C | S | 0 | 0 | 0 | 0 |
| 523 | C | T | 0 | 0 | 0 | 0 |
| Mean | | | 0.0 | 0.0 | 0.0 | 0% |
| +/−s.d. | | | 0.0 | 0.0 | 0.0 | 0% |
| 381 | D | I | 0 | 0 | 0 | 0 |
| 234 | D | N | 0 | 0 | 0 | 0 |
| 412 | D | F | 0 | 0 | 0 | 0 |
| 515 | D | E | 0 | 0 | 0 | 0 |
| 411 | D | S | 0 | 0 | 0 | 0 |
| 312 | D | T | 0 | 0 | 0 | 0 |
| Mean | | | 0.0 | 0.0 | 0.0 | 0% |
| +/−s.d. | | | 0.0 | 0.0 | 0.0 | 0% |

Results

The weight ranges, means and standard deviations for the three groups of treated dogs conformed to the label weight groupings of each product and the mean group weights were at similar loci within each group range. The mean cyphenothrin dose rate for Group B was 48.1 mg/kg. The mean group cyphenothrin and fipronil dose rates to the dogs in Group C were, respectively, 4.7 and 8.9 mg/kg. The toxicant active dose rates to the dogs in Group D were 80.1 mg/kg of etofenprox and 13.4 mg/kg of piperonyl butoxide (synergist). The presence and dose rates of the insect growth regulators (pyriproxyfen and methoprene) were ignored since these compounds are not know to have any effect on the ability of fleas to infest and survive on treated dogs.

Mean group efficacy values are summarized in Tables 14-19 showing both methods of calculating efficacy, "Eff#1" in red type and "Eff#2" in black type. Cells having efficacy values that meet or exceed the EPA's threshold for approval of label claims (90%) are in bold type and highlighted in yellow.

Mean group efficacy values (+/− standard deviation) were calculated from the aggregate individual percentage efficacy values. Group efficacy (mean+/− standard deviation) values are summarized in Tables 14-19.

The individual data on blood feeding by killed and repelled fleas are summarized in Tables 20-24.

The estimates for the shedding of flea eggs by the treated and control groups of dogs onto the tray liners at 5 and 15 minutes and at 1 and 4 hours are shown in Tables 25-29.

Statistical analyses (Student's "T" test) to determine the significance of apparent differences in flea and tick counts between the two groups of treated dogs and between the groups and the control group, used the statistical program in Microsoft® Office Professional 2003, version SP3. Probability values less than 0.05 were considered to show statistical significance. Exact probability values were entered down to <0.0001.

Flea Results

Against Existing Flea Burdens

Five minutes after treatment, all 3 products tested showed 50% or higher reduction in live flea counts, compared with the untreated controls, exceeding 70% efficacy at 15 minutes. By 1 hour, the efficacies of test substances used in Groups B and C exceeded the EPA threshold (90%) and the flea counts on Group B dogs were significantly smaller than on the Group C dogs. By 4 hours all 3 products were close to 100% effective.

Based on these data, all 3 products "start killing fleas in less than 5 minutes after application." The Group B substance and Group D "kill and repel existing fleas in less than 1 hour after application," while the Group B substance "kills and repels existing fleas in less than 4 hours after application."

Against New Fleas on Day 7

Five minutes after re-infestation with new fleas on day 7, reductions in mean group live flea counts on all treated dogs exceeded 50%, supporting that each product "starts killing new fleas by 5 minutes." At 15 minutes, the reductions in live flea counts on the dogs of Groups B and C were 90% to 100% and the flea burdens on these dogs were significantly smaller than the flea burdens on Group D dogs. Each of the products used in Groups B and C, based on the day 7 data, "kills and repels new fleas in less than 15 minutes", while the Group D product "kills and repels new fleas in less than 1 hour."

Against New Fleas on Day 14

Five minutes after re-infestation with new fleas on day 14, reduction of 50% in mean group live flea counts occurred on only the dogs of Group B, hence, this product "starts killing new fleas by 5 minutes." At 15 minutes, the reductions in live flea counts on the dogs of Groups B and D exceeded 90% supporting that each of these 2 products "kills and repels new fleas in less than 15 minutes." Not until 4 hours after re-infestation did the reduction in live flea counts on the dogs of Group C attain 90%, supporting the statement that this product "starts killing new fleas by 1 hour" and "kills and repels new fleas in less than 4 hours."

Against New Fleas on Day 21

Five minutes after re-infestation with new fleas on day 21, reduction of 50% in mean group live flea counts occurred on only the dogs of Group B, supporting the statement that this product "starts killing new fleas by 5 minutes." At 15 minutes, the reductions in live flea counts on the dogs of the other 2 groups exceeded 50% supporting that each of these 2 products "starts killing new fleas by 15 minutes." At 1 hour after re-infestation, reduction in live flea counts on the dogs of Group B exceeded 90% supporting that this product "kills and repels new fleas in less than 1 hour." By 4 hours after re-infestation, the efficacies of the 2 other products (Groups C and D) exceeded 90% supporting a statement that each of these 2 products "kills and repels new fleas in less than 4 hours." In addition, at 5 and 15 minutes and at 1 hour the flea burdens on the dogs treated with the Group B substance were significantly smaller than the burdens on the dogs treated with the Group C substance and similarly compared with the flea burdens on the dogs treated in Group D, but at only 15 minutes.

Against New Fleas on Day 28

Five minutes after re-infestation with new fleas on day 28, reduction of 50% in mean group live flea counts occurred on the dogs of all groups, supporting that each product "starts killing new fleas by 5 minutes" for all products. At 15 minutes after re-infestation, reduction in live flea counts on the dogs of Group B exceeded 90% supporting that this product "kills and repels new fleas in less than 15 minutes." By 1 hour after re-infestation, the efficacies of the 2 other products (Groups C and D) exceeded 90% supporting the statement that each of these products "kills and repels new fleas in less than 1 hour." In addition, at 15 minutes and at 1 hour the flea burdens on the dogs treated in Group B were significantly smaller than the burdens on the dogs treated in Group C and similarly compared with the flea burdens on the dogs treated in Group D, but at only 1 hour.

Against New Fleas on Day 35

Fifteen minutes after re-infestation with new fleas on day 35, reductions of 50% in mean group live flea counts occurred on the dogs of all groups, supporting that each product "starts killing new fleas by 15 minutes" for all products. At 1 hour after re-infestation, reduction in live flea counts on the dogs of Group B and on the dogs in Group D exceeded 90% supporting that each of these two products "kills and repels new fleas in less than 1 hour." By 1 hour after re-infestation, the efficacies of the Group C product and Group D product exceeded 90% supporting that each of these 2 products "kills and repels new fleas in less than 1 hour." At 4 hours reductions in flea counts on the treated dogs of Group C exceeded 90%, supporting that this product "kills and repels new fleas in less than 4 hours."

Summary of Flea Results

Assuming that, in order to support the statements "starts killing" and "kills and repels," the thresholds of 50% and 90% reductions, respectively, must be met for every time point, then, based on these data for fleas the 3 products may be summarized as follows:

Group B Product (20% Cyphenothrin/4% Pyriproxyfen):
"starts killing existing fleas in less than 5 minutes after application"
"starts killing new fleas by 5 minutes"
"kills and repels existing fleas in less than 1 hour after application"
"kills and repels new fleas in less than 15 minutes"

Group C Product (5.2% Cyphenothrin/9.8% Fipronil):
"starts killing existing fleas in less than 5 minutes after application"
"starts killing new fleas by 15 minutes"
"kills and repels existing fleas in less than 4 hours after application"
"kills and repels new fleas in less than 4 hours"

Group D Product (30% Etofenprox/5% Piperonyl Butoxide/3.6% (s)-Methoprene):
"starts killing existing fleas in less than 5 minutes after application"
"starts killing new fleas by 15 minutes"
"kills and repels existing fleas in less than 1 hour after application"
"kills and repels new fleas in less than 4 hours"

Conclusions for Flea Results

The results show superiority in starting to kill new fleas and kills and repels new fleas for the Group B product.

Tick Results

Against Existing Tick Burdens

Fifteen minutes after treatment, only the Group B and Group C products showed 50% or higher reduction in live tick counts, compared with the untreated control. At 15 minutes the tick counts on the Groups B and C dogs were significantly smaller than on the Group D dogs. By 4 hours, the efficacies of both test substances in Groups B and C exceeded the EPA threshold (90%). The Group D product did not achieve 50% reduction until 1 hour after treatment and did not attain 90% reduction in tick burdens before 24 hours after treatment.

Based on these data, both the Group B and Group C products "starts killing ticks in less than 15 minutes after application" and "kills and repels existing ticks in less than 4 hours after application." The Group D product "starts killing ticks in less than 1 hour after application" but does not "kill and repel existing ticks" since the 4 hour data is inadequate.

Against New Ticks on Day 7

Five minutes after re-infestation with new ticks on day 7, reduction in mean group live tick counts on dogs treated with both Group B and C products exceeded 50%, supporting that both of these products "starts killing new ticks by 5 minutes." At 15 minutes, the reductions in live tick counts on the dogs of these groups were 90% to 100%. The tick burdens on these dogs were highly significantly smaller than the tick burdens on Group D dogs throughout the first 4 hours after re-infestation. The Group D product did not achieve 50% reduction until 1 hour and did not attain 90% reduction in tick burdens before 24 hours after treatment. Both of the Group B and C products, based on the day 7 data, each "kills and repels new ticks in less than 15 minutes." The Group D product "starts killing ticks in less than 1 hour" but does not "kill and repel existing ticks" since the 4 hour data is inadequate.

Against New Ticks on Day 14

Five minutes after re-infestation with new ticks on day 14, reduction of 50% in mean group live flea counts occurred on the dogs of all 3 treated groups, supporting that each product "starts killing ticks by 5 minutes." At 15 minutes, the reductions in live tick counts on the dogs of Groups B and D exceeded 90% supporting that both of these 2 products "kills and repels new ticks in less than 15 minutes." Not until 4 hours after re-infestation did the reduction in live tick counts on the dogs of Group D attain 90% supporting that this product "kills and repels new ticks in less than 4 hours."

Against New Ticks on Day 21

Fifteen minutes after re-infestation with new ticks on day 21, reduction of greater than 50% in mean group live tick counts occurred on the dogs of Groups B and C, supporting that both of these products "starts killing new ticks by 15 minutes." Additionally, this reduction in Group B counts exceeded 90% supporting that the Group B product "kills and repels new ticks in less than 15 minutes." Not until 1 hour was the live tick count on the Group D dogs reduced below 50%, supporting that this product "starts killing new ticks by 1 hour." The live tick counts on the Group D dogs treated with the etofenprox-based product did not reach 90% even after 2 days. This result would deny the etofenprox-based product a quick kill/repellency claim and any efficacy assertion against ticks applied on day 21. In addition from 15 minutes on day 21 onwards the tick burdens on the dogs treated the etofenprox-based product (Group D) were significantly larger than the burdens on the dogs treated with either of the cyphenothrin-based Group B or Group C products.

Against New Ticks on Day 28

Five minutes after re-infestation with new fleas on day 28, reduction of 50% in mean group live flea counts occurred on the dogs of all 3 treated groups, supporting that each product "starts killing new ticks by 5 minutes." At 15 minutes after re-infestation, reduction in live tick counts on the dogs of Group B exceeded 90%, supporting that this product "kills and repels new ticks in less than 15 minutes." By 1 hour after re-infestation, the efficacy of the Group C product exceeded 90% supporting that this product "kills and repels new ticks in less than 1 hour." Not until 48 hours after re-infestation with new ticks did efficacy of the Group D product attain the 90% threshold. Although this data could support efficacy against ticks applied on day 21, it does not support any claim of quick kill/repellency for the Group D product against ticks applied on day 21. In addition from day 21 at 15 minutes, 1 and 4 hours, the tick burdens on the dogs treated with the Group B product were significantly smaller than the burdens on the dogs treated with the Group D product and at 1, 4 and 24 hours similarly for the Group C product.

Against New Ticks on Day 35

Fifteen minutes after re-infestation with new ticks on day 35, reduction of 50% in mean group live tick counts occurred on the dogs treated with the Group B product, supporting that this product "starts killing new ticks by 15 minutes." By 1 hour after re-infestation, the efficacy of the Group B product exceeded 90% supporting that this product "kills and repels new ticks in less than 1 hour." At 1 hour after re-infestation, reduction in live tick counts on the dogs of Groups C and D exceeded 50% supporting that both of these products "starts killing new ticks by 1 hour." At 4 hours reductions in tick counts on the treated dogs of Group C exceeded 90%, supporting that the Group C product "kills and repels new tick in less than 4 hours." The data does not support any quick kill/repellency claim for the Group D product after day 14.

Summary of Tick Results

Assuming that, to support "starts killing" and "kills and repels" ticks, the thresholds of 50% and 90% reduction, respectively, must be met for every time point, then based on these data for ticks, the three products may be summarized, as follows:

Group B Product (20% Cyphenothrin/2% Pyriproxyfen:
"starts killing existing ticks in less than 15 minutes after application"
"starts killing new ticks by 15 minutes"
"kills and repels existing ticks in less than 1 hour after application"
"kills and repels new ticks in less than 15 minutes"

Group C Product (5.2% Cyphenothrin/9.8% Fipronil):
"starts killing existing ticks in less than 15 minutes after application"
"starts killing new ticks by 15 minutes"
"kills and repels existing ticks in less than 4 hours after application"
"kills and repels new ticks in less than 4 hours"

Group D Product (30% Etofenprox/5% Piperonyl Butoxide/3.6% s-Methoprene):
"starts killing existing ticks in less than 1 hour after application"
"starts killing new ticks by 1 hour"
Does not kill or repel existing ticks
Does not kill or repel new ticks Conclusions for Tick Results As can be seen from the empirical data presented above, only treatment with the cyphenothrin-based combinations resulted in greater average kill rates and speed of kill for ticks at 15 minutes 1 hour, and 4 hours following treatment when compared to the etofenprox-based combination, and superior kill rates with the cyphenothrin-based combinations persisted after subsequent reinfestations of the host dogs with both fleas and ticks, up to 6 weeks after the initial application of the spot-on compositions.

Blood Feeding by Fleas

Blood feeding data from killed and repelled fleas up to 4 hours after re-infestation with new fleas on days 7, 14, 21, 28 and 35 were collected. For 28 days/1 month, none of the killed and repelled fleas collected below the cages contained any blood. The higher level of cyphenothrin in the Group B product had completely prevented any of the new fleas from taking a blood meal before they were killed or repelled. The lower level of cyphenothrin, accompanied by fipronil, in the Group C product reduced the ability of new fleas from taking blood, compared with the etofenprox-based product in Group D.

Egg Laying by Fleas

The data on flea egg collection during the first 4 hours after re-infestation showed that none of the new fleas were able to lay any eggs within this period of time. In contrast, the new fleas on the control dogs produced substantial quantities of eggs, which number increased between the 5 minute and the 4 hour time points. The numbers of eggs shed by the control dogs at 5 and 15 minutes were similar and small, indicating that these were likely to be residual eggs in the control dogs' coats from the previous infestation while the increase at 1 and 4 hours were likely new eggs just laid by the recently acquired fleas.

The conclusion from these data is that all 3 products were equally effective in preventing new fleas from producing eggs before they died during the 4 hours after infestation.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the following claims.

What is claimed is:

1. A method for reducing the incidence of flea allergy dermatitis in a companion animal by reducing blood feeding by ectoparasites on the companion animal by at least 80%, the method comprising: administering a composition comprising up to about 50% (w/w) cyphenothrin and about 50% to about 85% (w/w) organic solvent, wherein the composition is administered in a volume sufficient to deliver a dosage of cyphenothrin ranging from about 0.1 mg/kg to about 40 mg/kg of animal weight.

2. The method of claim 1, wherein composition is a spot-on composition.

3. The method of claim 2, wherein the method further comprises administering a localized cutaneous application of the spot-on composition between the shoulders of the companion animal.

4. The method of claim 1, wherein blood feeding by ectoparasites is reduced by at least 90%.

5. The method of claim 1, wherein the ectoparasite is a flea.

6. The method of claim 5, wherein the flea is *Ctenocephalides felis*.

7. The method of claim 1, wherein the composition comprises between about 20% to about 30% (w/w) cyphenothrin.

8. The method of claim 1, wherein the composition is administered as a one-time treatment.

9. The method of claim 1, wherein the composition is administered once every five weeks.

10. The method of claim 1, wherein the composition is administered once every six weeks.

11. The method of claim 1, wherein the companion animal is a dog.

12. The method of claim 1, wherein the composition further comprises about 1% to about 10% (w/w) of an antioxidant.

13. The method of claim 12, wherein the antioxidant comprises a vitamin E compound.

14. The method of claim 12, wherein the antioxidant is selected from the group consisting of tocopherol acetate, tocopherol linoleate, tocopherol nicotinate, tocopherol succinate, ascorbyl tocopherol phosphate, dioleyl tocopherol methylsilanol, tocophersolan, tocopherol linoleate/oleate, and combinations thereof.

15. The method of claim 14, wherein the antioxidant is tocopherol nicotinate.

16. The method of claim 1, wherein the composition further comprises about 1% to about 10% (w/w) of an insect growth regulator.

17. The method of claim 1, wherein the composition comprises about 1% to about 5% (w/w) of an insect growth regulator.

18. The method of claim 17, wherein the insect growth regulator is a juvenile hormone mimic selected from the group consisting of fenoxycarb, hydroprene, kinoprene, methoprene, pyriproxyfen, triprene, and combinations thereof.

19. The method of claim 13, wherein the insect growth regulator is pyriproxyfen.

20. The method of claim 1, wherein the composition comprises between about 1% to about 50% (w/w) cyphenothrin.

21. The method of claim 1, wherein the organic solvent comprises diethylene glycol monoethyl ether.

22. The method of claim 1, wherein the composition is administered once every four weeks.

23. A method of reducing the incidence of flea allergy dermatitis in a companion animal by reducing blood feeding by ectoparasites on the companion animal by at least 80%, the method comprising: administering a composition comprising up to about 50% (w/w) cyphenothrin, up to about 5% (w/w) insect growth regulator, and about 50% to about 85% (w/w) diethylene glycol monoethyl ether, wherein the composition is administered once every four weeks in a volume sufficient to deliver a dosage of cyphenothrin ranging from about 0.1 mg/kg to about 40 mg/kg of animal weight.

24. A method of reducing the incidence of flea allergy dermatitis in a companion animal by reducing blood feeding by ectoparasites on the companion animal by at least 80%, the method comprising: administering a composition comprising about 20% (w/w) cyphenothrin, about 2% (w/w) pyriproxyfen, and about 78% (w/w) diethylene glycol monoethyl ether, wherein the composition is administered once every four weeks in a volume sufficient to deliver a dosage of cyphenothrin ranging from about 0.1 mg/kg to about 40 mg/kg of animal weight.

25. A method of reducing the incidence of flea allergy dermatitis in a companion animal by reducing blood feeding by ectoparasites on the companion animal by at least 80%, the method comprising: administering a composition comprising about 30% (w/w) cyphenothrin, about 2% (w/w) pyriproxyfen, and about 68% (w/w) diethylene glycol monoethyl ether, wherein the composition is administered once every four weeks in a volume sufficient to deliver a dosage of cyphenothrin ranging from about 0.1 mg/kg to about 40 mg/kg of animal weight.

26. A method of reducing the incidence of flea allergy dermatitis in a dog weighing between 11 and 20 pounds by reducing blood feeding by ectoparasites on the dog by at least 80%, the method comprising:
(a) removing one 4.0 mL tube containing a composition comprising about 30% (w/w) cyphenothrin, about 2% (w/w) pyriproxyfen, and about 68% (w/w) diethylene glycol monoethyl ether from a package;
(b) opening the tube to form an open end of the tube;
(c) placing the open end of the tube onto the dog's skin; and
(d) squeezing the tube to apply the composition to the dog's skin.

27. The method of claim 26, further comprising disposing of the tube in a trash receptacle after application of the composition to the dog.

28. The method of claim 26, wherein the open end of the tube is placed on a starting location high on the back of the dog's neck.

29. The method of claim 28, further comprising squeezing the tube to deposit the composition as a stripe from the starting location to an ending point.

30. The method of claim 29, wherein the ending point is midway between the dog's neck and tail.

31. The method of claim 26, further comprising repeating the method once every four weeks.

32. A method of reducing the incidence of flea allergy dermatitis in a dog weighing between 21 and 39 pounds by reducing blood feeding by ectoparasites on the dog by at least 80%, the method comprising:

(a) removing one 3.0 mL tube containing a composition comprising about 30% (w/w) cyphenothrin, about 2% (w/w) pyriproxyfen, and about 68% (w/w) diethylene glycol monoethyl ether from a package;
(b) opening the tube to form an open end of the tube;
(c) placing the open end of the tube onto the dog's skin; and
(d) squeezing the tube to apply the composition to the dog's skin.

33. A method of reducing the incidence of flea allergy dermatitis in a dog weighing between 40 and 60 pounds by reducing blood feeding by ectoparasites on the dog by at least 80%, the method comprising:
(a) removing one 4.5 mL tube containing a composition comprising about 30% (w/w) cyphenothrin, about 2% (w/w) pyriproxyfen, and about 68% (w/w) diethylene glycol monoethyl ether from a package;
(b) opening the tube to form an open end of the tube;
(c) placing the open end of the tube onto the dog's skin; and
(d) squeezing the tube to apply the composition to the dog's skin.

34. A method of reducing the incidence of flea allergy dermatitis in a dog weighing at least 61 pounds by reducing blood feeding by ectoparasites on the dog by at least 80%, the method comprising:
(a) removing one 6.0 mL tube containing a composition comprising about 30% (w/w) cyphenothrin, about 2% (w/w) pyriproxyfen, and about 68% (w/w) diethylene glycol monoethyl ether from a package;
(b) opening the tube to form an open end of the tube;
(c) placing the open end of the tube onto the dog's skin; and
(d) squeezing the tube to apply the composition to the dog's skin.

* * * * *